United States Patent
Delmore et al.

(10) Patent No.: US 6,595,938 B1
(45) Date of Patent: *Jul. 22, 2003

(54) ARTICLE HAVING SOFT AND HARD REGIONS

(75) Inventors: Michael D. Delmore, Moundsview, MN (US); Jason R. Riley, Duluth, MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/132,255

(22) Filed: Aug. 11, 1998

Related U.S. Application Data

(63) Continuation-in-part of application No. 08/672,012, filed on Jun. 24, 1996, now Pat. No. 5,807,292.

(51) Int. Cl.[7] ................................................ A61F 5/00
(52) U.S. Cl. .............................................. 602/8; 602/1
(58) Field of Search ........................................ 602/6–8

(56) References Cited

U.S. PATENT DOCUMENTS

| | | |
|---|---|---|
| 2,919,467 A | 1/1960 | Mercer |
| 3,252,181 A | 5/1966 | Hureau |
| 3,630,194 A | 12/1971 | Boardman |
| 3,908,644 A | 9/1975 | Neinart et al. |
| 4,131,114 A | 12/1978 | Kirkpatrick et al. |
| 4,152,479 A | 5/1979 | Larsen |
| 4,309,990 A | 1/1982 | Brooks et al. |
| 4,351,683 A | 9/1982 | Kusilek |

(List continued on next page.)

FOREIGN PATENT DOCUMENTS

| | | |
|---|---|---|
| EP | 0 135 890 | 4/1985 |
| EP | 0 407 056 | 1/1991 |
| WO | WO 95/13039 | 5/1995 |

OTHER PUBLICATIONS

Carl R. Noller, Chemistry of Organic Compounds, Second Edition, pp. 121, 122 (1957).
ASTM Designation: D5342–93, Standard Test Method for rEsistance to bending of Paper and Paperboard (Taber–Type Tester), pp. 800–802.
V–5 Stiffens Tester Instruction Manual, Teledyne Taber, 6/79.

Primary Examiner—Brian L. Casler
Assistant Examiner—Michael M Thompson
(74) Attorney, Agent, or Firm—Mueting, Raasch & Gebhardt, PA

(57) ABSTRACT

The present invention provides an orthopedic casting article and a protective pad article having soft edges. In one embodiment, the article comprises a flexible sheet material impregnated or coated with two different resins. In an alternative embodiment, the article comprises an extruded sheet material comprising two different extruded materials. One of the resins or extruded materials is soft or resilient compared to the other resin or material. By selectively providing the softer materials at defined regions of the article the hardness of the region can be adjusted. The article may be in the form of an orthopedic casting tape or a protective pad comprising a fabric backing that is longitudinally impregnated or coated with two different curable resins. A harder, first curable resin is used to coat a longitudinally extending center region of the fabric backing; and a softer, second curable resin is used to coat at least one longitudinally extending edge region of the fabric backing. When the casting tape is wrapped around a limb the softer edge regions may be overlapped to form a soft, comfortable edge of the cured cast.

30 Claims, 7 Drawing Sheets

U.S. PATENT DOCUMENTS

| | | |
|---|---|---|
| 4,376,438 A | 3/1983 | Straube et al. |
| 4,384,022 A | 5/1983 | Fowler |
| 4,411,262 A | 10/1983 | von Bonin et al. |
| 4,433,680 A | 2/1984 | Yoon |
| 4,483,332 A * | 11/1984 | Rind .............................. 602/8 |
| 4,502,479 A | 3/1985 | Garwood et al. |
| 4,609,578 A | 9/1986 | Reed |
| 4,628,917 A | 12/1986 | Campagna, Jr. et al. |
| 4,631,215 A | 12/1986 | Welygan et al. |
| 4,631,215 A | 12/1986 | Welygan et al. |
| 4,634,485 A | 1/1987 | Welygan et al. |
| 4,634,485 A | 1/1987 | Welygan et al. |
| 4,667,661 A | 5/1987 | Scholz et al. |
| 4,668,563 A | 5/1987 | Buese et al. |
| 4,683,877 A | 8/1987 | Ersfeld et al. |
| 4,705,840 A | 11/1987 | Buckanin |
| 4,794,937 A | 1/1989 | Hofmann |
| 4,899,738 A | 2/1990 | Parker |
| 4,946,726 A | 8/1990 | Sandvig et al. |
| 4,968,542 A | 11/1990 | Gasper et al. |
| 5,014,403 A | 5/1991 | Buese |
| 5,027,803 A | 7/1991 | Scholz et al. ............. 128/89 R |
| 5,346,939 A | 9/1994 | Moren et al. ............... 524/176 |
| 5,353,486 A | 10/1994 | Schmidt et al. ................ 28/168 |
| 5,354,259 A | 10/1994 | Scholz et al. .................. 602/8 |
| 5,364,693 A | 11/1994 | Moren et al. ............... 428/263 |
| 5,405,643 A | 4/1995 | Scholz ...................... 427/2.31 |
| 5,409,448 A | 4/1995 | Kelley ........................... 620/5 |
| 5,423,735 A | 6/1995 | Callinan et al. ............... 602/8 |
| 5,454,780 A | 10/1995 | Duback et al. ................ 602/8 |
| 5,456,658 A | 10/1995 | Duback et al. ................ 602/8 |
| 5,468,219 A * | 11/1995 | Crippen ....................... 602/6 |
| 5,474,522 A | 12/1995 | Scholz et al. .................. 602/8 |
| 5,603,691 A * | 2/1997 | Scholz et al. .................. 602/8 |
| 5,807,292 A * | 9/1998 | Delmore ....................... 602/8 |

* cited by examiner

ARTICLE HAVING SOFT AND HARD REGIONS

This application is a continuation-in-part of application Ser. No. 08/672,012 filed on Jun. 24, 1996 now U.S. Pat. No. 5,807,292.

FIELD OF THE INVENTION

This invention relates to orthopedic casting materials and protective pads.

BACKGROUND OF THE INVENTION

Many different articles have been developed for use as orthopedic casting materials in the immobilization of broken or otherwise injured body limbs and for use as protective pads to protect against impact injuries while participating in a physical activity such as an athletic event. Some of the first casting materials developed for this purpose involved the use of plaster of Paris bandages consisting of a cotton gauze mesh fabric with plaster incorporated into the openings and onto the surface of the mesh fabric. Plaster of Paris casts, however, have a number of attendant disadvantages, including a low strength-to-weight ratio, resulting in a finished cast which is very heavy and bulky. In addition, plaster of Paris casts develop their strength over a relatively long period of time, thus making it necessary to avoid weight bearing situations for up to 24 to 48 hours. Furthermore, plaster of Paris casts typically disintegrate in water, thus making it necessary to avoid bathing, showering, or other activities involving contact with water.

A significant advancement in the art was achieved when synthetic polyisocyanate prepolymers were found to be useful in formulating a resin for orthopedic casting materials and for preparation of protective pads. Typical commercially available synthetic orthopedic casting materials comprise a knit fiberglass fabric backing impregnated with a polyisocyanate prepolymer resin. These orthopedic casting materials can provide significant advancement over the plaster of Paris casts, including a higher strength-to-weight ratio. However, knitted fiberglass backings of conventional casting articles or protective pads may become quite rough when cured and often produce casts or protective pads with sharp edges. The sharp edges can cause skin abrasions, skin irritation and/or snag clothing. As a result, the health care worker or athletic event participant has had to employ padding materials at the edges to attempt to avoid contact of the casting article or protective pad with the skin.

SUMMARY OF THE INVENTION

From the foregoing, it will be appreciated that what is needed in the art is an orthopedic casting material which has the benefits of synthetic orthopedic casting materials, e.g., high strength-to-weight ratio, but without the sharp edges. Such orthopedic casting materials and methods for preparing the same are disclosed and claimed herein.

In general, the orthopedic casting tapes of the present invention comprise a first longitudinally extending region of a soft casting material and a second longitudinally extending region of a hard casting material that is connected to the first region. The soft and hard casting materials may comprise, for example, soft or hard curable resins associated with a backing, soft or hard thermoplastic materials associated with a backing, or soft or hard extruded casting materials.

In one preferred embodiment, the present invention provides orthopedic casting tapes comprising a backing and at least one curable resin associated with the backing. The casting tape includes at least one longitudinally extending region of a soft casting material and at least one longitudinally extending region of a hard casting material. Preferably, the longitudinally extending region of soft casting material and the longitudinally extending region of hard casting material comprise different curable resins. Alternatively, they may comprise two different backings.

The casting tapes most preferably have one or two edge regions of the softer casting material. When wrapped about a limb, the soft edge regions may form a soft edge of the cast. For a typical 10 cm wide casting tape, the soft edge regions are preferably at least 0.5 cm wide.

The invention also describes novel methods of making orthopedic casts including the steps of: providing a curable casting tape having at least one longitudinally extending region of a soft casting material and at least one longitudinally extending region of a hard casting material; initiating the cure of the casting tape (e.g., by exposing the casting tape to water); optionally wrapping the casting tape so that the soft region overlaps at one or more edges of the cast; and allowing the casting tape to cure to form an orthopedic cast.

The invention also describes novel manufacturing methods for making these new orthopedic casting tapes. In one embodiment, these new methods include the steps of providing a fabric backing; and coating two different curable resins on the backing to form two adjacent longitudinally extending regions having differential hardness.

The present invention also provides improved splint articles comprising, e.g., a backing and at least one curable resin associated with the backing. In general, the splint article has a hard center region and at least one soft edge region. The splint may further comprise a thumb hole having a soft edge region surrounding the periphery of the thumb hole.

The present invention also provides improved protective padding articles comprising, e.g., a backing and at least one curable resin associated with the backing. In general, the protective pad article has a hard center region and at least one soft region. The protective pad can be custom-fitted to a portion of the human body for protection against impact injuries.

DEFINITIONS

A "casting material" refers to a material (e.g., a composite material, a resin coated sheet, etc.) that undergoes a change of state from a generally moldable first state to a generally nonmoldable second state, thereby allowing the formation of a customizable support device. The support devices of the present invention are characterized as having at least one "soft region" and at least one "hard region." The second states of the soft region and the hard region differ in at least one physical property, with the hard region being at least discernibly more rigid, less resilient or harder than the soft region. The term "differential hardness" refers to the relative difference in rigidity, resilience, or hardness between the soft and hard regions of a casting tape or splint (i.e., the relative difference between the second states of the two regions).

A "protective pad" is a form of casting material that, while in the moldable first state, can be custom-fitted to a portion of the human body. After changing to the nonmoldable second state, the protective pad is secured to the human body for protection against impact injuries.

A "casting tape" refers to an elongated strip of a casting material. The casting tapes of the present invention may be optionally wound on a roll prior to use and are characterized as having at least one longitudinally extending "soft region" and at least one longitudinally extending "hard region." The second states of the soft region and the hard region differ in at least one physical property, with the hard region being at least discernibly more rigid, less resilient or harder than the soft region.

The "soft region" of a casting material (e.g., casting tape, splint or protective pad) is that region of the casting material that comprises a soft casting material. A "soft casting material" preferably refers to a casting material that undergoes a change of state from a generally moldable first state to a second state comprising a generally semi-rigid, resilient, or soft support device. A soft casting material includes a soft resin coated on a backing, as well as a soft extruded casting material. A "soft resin" preferably refers to a curable resin system that, when coated or otherwise applied onto a backing and cured, forms a generally semi-rigid, resilient, or soft support device. More preferably, the soft resin, when coated and cured onto the edge of a traditional fiberglass backing, provides an edge that doesn't cut and/or abrade the wearer's skin or otherwise hurt the wearer.

The "hard region" of a casting material (e.g., casting tape, splint or protective pad) is that region of the casting material that comprises a hard casting material. A "hard casting material" preferably refers to a casting material that undergoes a change of state from a generally moldable first state to a second state comprising a generally rigid, non-resilient, or hard support device. A hard casting material includes a hard resin coated on a backing, as well as a hard extruded casting material. A "hard resin" preferably refers to a curable resin system that, when coated or otherwise applied onto a backing and cured, forms a generally rigid, non-resilient, or hard support device. More preferably, the hard resin, when coated and cured onto a traditional fiberglass backing, provides a rigid support device that can support the weight normally carried by the limb around which the support device is wrapped.

A "curable resin system" refers to any type of resin system that undergoes a change of state from a generally flowable or moldable uncured first state to a generally nonflowable or nonmoldable cured second state.

The terms "backing"; "carrier"; and "scrim" refer to the structure upon which one or more curable resins are coated or otherwise applied. A "fabric backing" is a backing that comprises a knit, woven or nonwoven fabric material.

The term "associated with" refers to the intimate relationship between the resin system and the backing, such as may be accomplished, for example, by coating a backing with a resin and/or impregnating a backing with a resin.

BRIEF DESCRIPTION OF THE DRAWINGS

The invention may be more clearly understood by reference to the drawings, wherein:

FIG. 7b shows a ring of cured casting material positioned in the test fixture of FIG. 7a.

In FIG. 1 a partially unwound roll 10 of casting tape 20 is shown in perspective view. The unwound portion of casting tape 20 is shown with a center region 12, a first edge region 14, and a second edge region 16. The partially unwound sheet is shown with a first edge 15, a second edge 17, and a first end 13. A second end 19 is wound around the core of the roll and is not in view. At least one of the first edge region 14 and second edge region 16 preferably exhibits a differential hardness from the center region 12. More preferably, at least one of the first edge region 14 and second edge region 16 is a soft region, that extends throughout the thickness of the tape and along its entire length and the center region 12 is a hard region. In a most preferred embodiment both the first edge region 14 and second edge region 16 are soft regions, and the center region 12 is a hard region.

In FIG. 2 a partially unwound roll of casting tape is shown in perspective view. The unwound portion of casting tape 120 is shown with a center region 112 and a first edge region 114. The partially unwound sheet is shown with a first edge 115, a second edge 117, and a first end 113. A second end 119 is wound around the core of the roll and is not in view. The first edge region exhibits a differential hardness from the center region 112. In a preferred embodiment the first edge region 114 is a soft region, and the center region 112 is a hard region.

In FIG. 3 a partially unwound roll 210 of casting tape 220 is shown in perspective view. The partially unwound sheet of casting tape 220 is shown with center regions 212, a first edge region 214, optional second edge region 216 and optional third region 218. The unwound portion is shown with a first edge 215, a second edge 217, and a first end 213. A second end 219 is wound around the core of the roll and is not in view. At least one of the first edge region 214, second edge region 216, or third region 218 exhibits a differential hardness from the center regions 212. In a preferred embodiment each of the first edge region 214, second edge region 216 and third region 218 are soft regions, and the center regions 212 are hard regions.

FIG. 4 illustrates a human arm wrapped with a casting tape of the present invention. As shown in FIG. 4 the casting tape 20 has a center region 12 and at least one edge region 14 running the length of the tape. If desired, an optional second edge region 16, having differential hardness, may also be utilized. When the casting tape 20 is wound in a spiral pattern, as shown in portion A, the edge region(s) 14, 16 overlaps the center region 12 of one or more adjacent windings or layers. However, if desired, an edge region 14, 16 may be overlapped against an edge region 14, 16 of one or more adjacent windings or layers. This may be accomplished, for example, at cast edges 22, 24, 26 and 28. If desired, the casting tape of FIG. 4 may be utilized beneficially by folding the tape in half when wrapping around the thumb at 24. When so folded, a portion of the center region (shown as 218 of FIG. 3) becomes an edge of the doubled over tape and preferably provides a tape 220 having a soft region along each edge.

FIG. 5a shows a splint article 310 having a center hard region 312 and a soft region 314 along the periphery of the splint article 310 and around a thumb hole 311. FIGS. 5b and 5c show the splint article 310 of FIG. 5a adapted to a human arm. An optional padding material 330 is wrapped or placed on the arm prior to placement of the splint article 310. FIG. 5d shows an overlay bandage 340 wrapped around the human arm and over the splint article 310 of FIGS. 5b and 5c, thereby securing the splint article 310 to the arm.

FIG. 6 shows an extruded casting article or casting tape 420 with two soft regions. In FIG. 6 a partially unwound roll 410 of casting tape 420 is shown in perspective view. The partially unwound extruded sheet of casting tape 420 is shown with a center region 412, a first edge region 414, and a second edge region 416. The unwound portion is shown with a first edge 415, a second edge 417, and a first end 413. A second end 419 is wound around the core of the roll and is not in view. At least one of the first edge region 414 and second edge region 416 preferably exhibits a differential hardness from the center region 412. More preferably, at least one of the first edge region 414 and second edge region 416 is a soft region, and the center region 412 is a hard region. In a most preferred embodiment both the first edge region 414 and second edge region 416 are soft regions each comprising at least one extruded element of a soft casting material, and the center region 412 is a hard region comprising at least one extruded element, preferably a plurality of extruded elements, of a hard casting material.

FIG. 7a illustrates a test fixture 700 used to support a ring of casting material 740 when measuring edge strength. The fixture comprises a base 710, a bottom support 720 positioned at a 45 degree angle to the base 710, and a side support 724 positioned at a 90 degree angle to the bottom support 720. As shown in FIG. 7b, a ring of casting material 740 is placed into the text fixture 700 with a first end of the ring 741 positioned against bottom support 720. A portion of the side of the cylindrical ring of casting material 740 rests against side support 724. Side support 724 comprises a machined surface that matches the radius of the ring of casting material 740. A cylindrical probe 744 is brought to bear against the upper leading edge 742 of the ring of casting material 740. The cylindrical probe 744 is attached to a testing apparatus 746 such as an Instron machine.

FIG. 8a illustrates side view of a three-piece slotted die 800 used to coat two or more resins onto a backing. The die is shown with two outer plates 820a and 820b, and a middle plate 810. As shown in FIGS. 8b and 8c, outer plates 820a and 820b comprise a plurality of bolt holes 812. Outer plate 820a further comprises feed holes 824, 826, and 828. Middle plate 810 comprises a plurality of bolt holes 812 and tapered flow cavities 814, 816, and 818 that are in communication with feed holes 824, 826, and 828, respectively. The tapered flow cavities direct the resin flow to provide coating widths E and C.

FIG. 9 shows a protective pad article 510 having a center hard region 512 and two soft edge regions 514.

Figure 1:
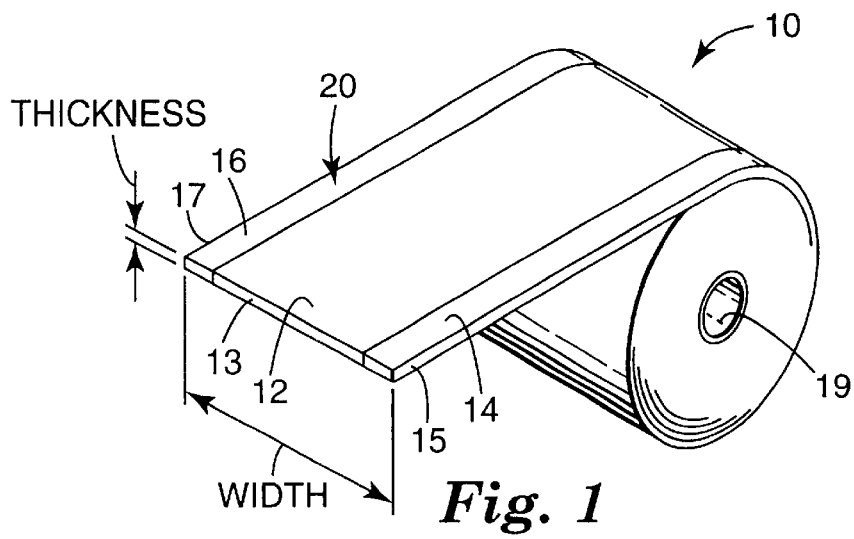
FIG. 1 shows a partially unwound roll of casting tape having two soft regions along each edge of the casting tape.
Figure 2:
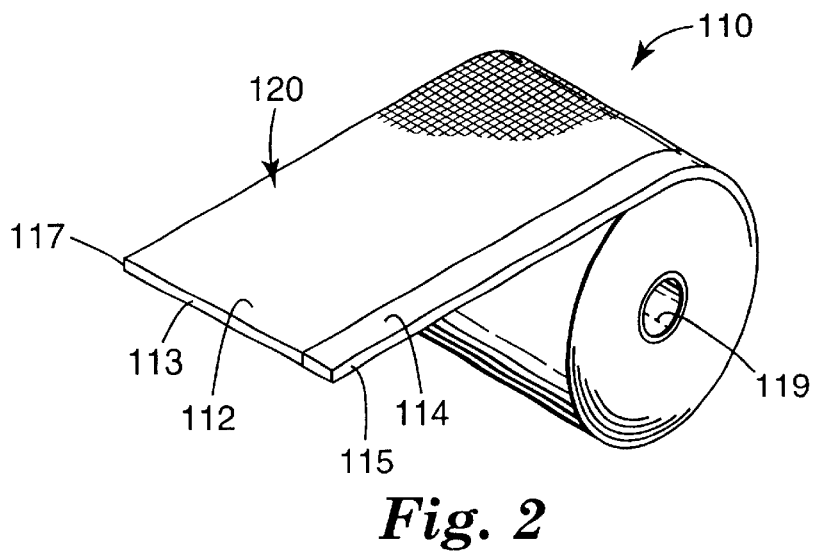
FIG. 2 shows a partially unwound roll of casting tape having one soft region along one edge of the casting tape.
Figure 3:
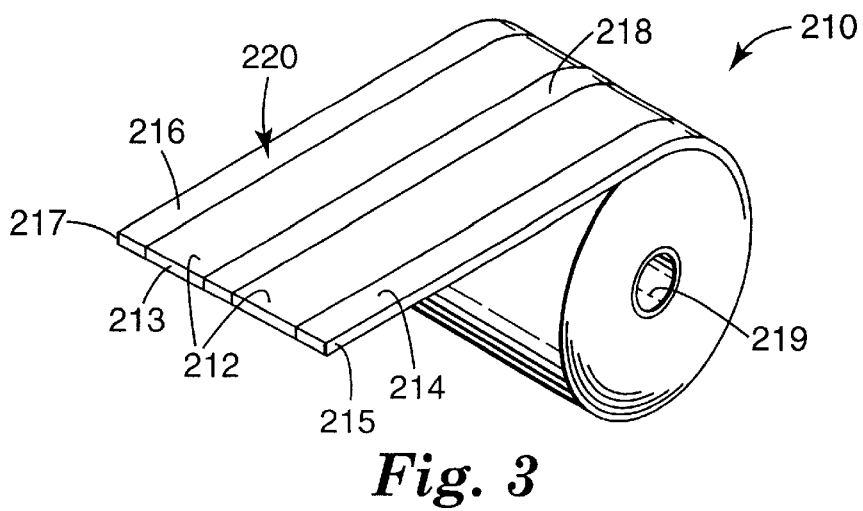
FIG. 3 shows a partially unwound roll of casting tape having three soft regions along each edge of the casting tape and down the center of the casting tape.

This invention utilizes certain principles and/or concepts as are set forth in the claims appended to this specification. Those skilled in the casting arts to which this invention pertains will realize that these principles and/or concepts are capable of being illustrated in a variety of embodiments which may differ from the exact embodiments utilized for illustrative purposes in this specification. For these reasons, the invention described in this specification is not to be construed as being limited to only the illustrative embodiments but is only to be construed in view of the appended claims.

DETAILED DESCRIPTION OF THE INVENTION

The present invention provides a curable orthopedic support article or a curable protective pad article having at least two regions having differential hardness. In one presently preferred embodiment, the support material or protective pad comprises a flexible sheet material associated with (e.g., impregnated or coated with) at least one liquid resin system which cures upon exposure to a curing or activating agent. The support material or protective pad preferably further comprises packaging means for preventing contact of the resin with the curing or activating agent prior to use. The invention also relates to the method of applying the support material, and to the cured device formed from the support material. The invention further relates to a method of making the support material.

In an alternative embodiment, the support material or protective pad comprises a flexible sheet material associated with (e.g., impregnated or coated with) at least one thermoplastic material which, upon cooling, changes from a first moldable state to a second shape retaining state. In a further alternative embodiment, the support material or protective pad comprises an extruded sheet material of either a thermoplastic material or a viscous curable material.

Preferably, the orthopedic support article is in the form of an orthopedic casting tape comprising a fabric backing that is associated with two different curable resins. A harder, first curable resin is associated with the center region of the fabric backing; and a softer, second curable resin is associated with at least one edge region of the fabric backing. More preferably, the casting tape comprises a center region of a traditional "hard" curable resin and two edge regions of a "soft" curable resin. When wrapped around a limb the softer edge regions may be overlapped to form a soft, comfortable edge of the cured cast.

Alternatively, the orthopedic support material may be in the form of a casting tape comprising a single resin that is impregnated or coated onto a fabric backing. In this embodiment, the fabric backing itself comprises at least two different materials or two different constructions of the same type of material. For example, the fabric may be knit using two different types of yarns. A first type of yarn (e.g., fiberglass) may be used to form a center region of the fabric while a second, softer type of yarn (e.g., polyester, cotton, rayon, polyolefin, polyurethane, etc.) may be used to form at least one edge region of the fabric. The softer edge yarns will provide a lower modulus cured fabric relative to the higher modulus fiberglass center yarns. The fabric may alternatively be knit using a single type of yarn but in a manner such that a first region of the fabric absorbs more or less of the curable resin. For example, the capacity of a wale yarn to absorb resin may be adjusted by increasing or decreasing the number of fibers in the wale yarn. In this manner, more or less resin can be directed to a particular wale, resulting in differential hardness of the resin impregnated cured fabric.

If desired, a combination of these techniques may be employed. For example, the orthopedic support material may be in the form of a casting tape comprising two different resins that are impregnated or coated onto a fabric backing comprising two different materials.

As previously mentioned, one or more curable resins may be associated with the backing. In one presently preferred embodiment, the casting tape comprises two different curable resin formulations. A harder, first curable resin formulation is used to coat the center region of the casting tape, and a softer, second curable resin formulation is used to coat at least one edge region of the casting tape. The first and second resin formulations may be similar, e.g., of the same chemical class, and differ only in their respective cured physical properties (e.g., both resins may be water-curable, isocyanate functional resins). Alternatively, the first and second resin formulations may be of diff&rent chemical classes. Preferably, the two resins are compatible and bond well to each other, e.g., when adjacent layers of the casting tape overlap and cause contact of the two resin formulations. Most preferably, the two resins comprise the same basic chemistry.

The curable resin used in the hard region of the casting material is preferably any curable resin which will satisfy the functional requirements of an orthopedic cast. Obviously, the resin must be nontoxic (e.g., not give off significant amounts of toxic vapors during curing which may be harmful to either the patient or the person applying the cast); and not cause skin irritation (e.g., either by chemical irritation or the generation of excessive heat during cure). Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid enough and strong enough to support loads and stresses to which the cast is subjected by the activities of the wearer.

The following disclosure relates primarily to the presently preferred embodiments of the invention wherein water-curable isocyanate-functional prepolymers are employed as the curable resin. Other suitable curable resins are discussed later.

Some presently more preferred hard resins for use in the present invention are water-curable, isocyanate-functional prepolymers. Suitable systems of this type are disclosed, for example, in U.S. Pat. Nos. 4,131,114; 4,376,438; 4,433,680; 4,411,262; and 4,502,479 which are herein incorporated by reference. Presently more preferred resin systems are disclosed in U.S. Pat. No. 4,667,661; and U.S. patent application Ser. Nos. 07/376,421 and 08/320,917 which are herein incorporated by reference.

A water-curable isocyanate-functional prepolymer as used herein means a prepolymer derived from a polyisocyanate compound and a reactive hydrogen compound or oligomer (e.g., a "polyol"). A reactive hydrogen compound is a compound having active hydrogen in accordance with the well known Zerevitinov test as described, for example, in *Chemistry of Organic Compounds* by Carl R. Noller, Chapter 6, pp. 121–122 (1957). The prepolymer has sufficient isocyanate-functionality to cure upon exposure to water, e.g., moisture vapor, or preferably liquid water.

It is presently preferred to employ a polyisocyanate prepolymer formed by the reaction of an isocyanate and a polyol.

Suitable isocyanates are disclosed, for example, in U.S. Pat. Nos. 4,376,438; 4,433,680; and 4,502,479, and include: 2,4-toluene diisocyanate, 2,6-toluene diisocyanate, and mixtures of these isomers; 4,4'-diphenylmethane diisocyanate, 2,4'-diphenylmethane diisocyanate, and mixtures of these isomers together with possible small quantities of 2,2'-diphenylmethane diisocyanate (typical of commercially available diphenylmethane diisocyanate); and aromatic polyisocyanates and mixtures such as are derived from phosgenation of the condensation product of aniline and formaldehyde. It is preferred to use an isocyanate which has low volatility such as diphenylmethane diisocyanate (MDI) rather than a more volatile material such as toluene diisocyanate (TDI). Suitable commercially available isocyanate starting materials include "ISONATE" 2143L (available from Dow Chemical Co.), "MONDUR" MRS (Mobay Chem. Co., Pittsburg, Pa.), and "PAPI" (Dow Chemical Co.).

Suitable polyols for use in the prepolymer system include polyalkylene oxides (e.g., polyethylene oxide and polybutylene oxide), polypropylene ether glycols (available from Arco Chemical under the tradename "ARCOL PPG"; and from BASF Wyandotte under the tradename "PLURACOL"), polytetramethylene ether glycols (e.g., "POLYMEG" from the Quaker Oats Co. or "TERATHANE" from the E.I.Du Pont de Nemours, Co., Wilmington Del.), polycaprolactone diols (e.g., "TONE" series of polyols from Union Carbide), and polyester polyols (e.g., hydroxyl terminated polyesters obtained from esterification of dicarboxylic acids and diols such as the "RUCOFLEX" polyols available from Ruco division, Hooker Chemical Co.). In general, by using lower molecular weight polyols, the rigidity of the cured resin can be increased.

An example of a "hard resin" useful in the casting material of the invention uses an isocyanate known as ISONATE™ 2143L available from the Dow Chemical Company (a mixture of di- and tri-isocyanates containing about 73% of MDI) and a polypropylene oxide polyol available from Arco Chemical known as ARCOL PPG725. To prolong the shelf life of the material, it is preferred to include from 0.01 to 1.0 percent by weight of benzoyl chloride or another suitable stabilizer (based on total resin weight).

To form a presently preferred hard resin, the isocyanates and the polyols are reacted with one another under conventional polyurethane reaction conditions known to those skilled in the art. The NCO:OH ratio of the reactants is preferably between 1.5:1 and 7:1 and more preferably between 2.5:1 and 4.5:1.

In general, the hardness of a resin may be affected by adjusting the "functionality" of the reactants. As the functionality increases, e.g., as the relative amount of polyfunctional material compared to di-functional material is increased, the hardness will increase. Also in general, the hardness of a resin may be affected by adjusting the "equivalent weight" of the reactants for a given NCO:OH ratio. As the equivalent weight increases, e.g., as the equivalent weight of polyol is increased, the hardness will decrease.

To form a presently preferred hard resin having an NCO:OH ratio in the range of 2.5:1 to 4.5:1, the theoretical isocyanate equivalent weight of the prepolymer (grams resin/equivalent isocyanate) preferably is less than about 1000 grams, more preferably less than about 500 grams, and most preferably less than about 400 grams. Preferably the theoretical polyol equivalent weight of the prepolymer is less than about 1000 grams, more preferably less than about 500 grams, and most preferably less than about 400 grams. Of course these weights might be different were the resin to contain an adjuvent such as a plasticizer or utilize a different NCO:OH ratio or average functionality of reactants.

One or more regions of the casting tape, e.g., one or both edge regions, preferably is coated with a "soft resin." Some presently more preferred soft resins for use in the present invention are water-curable, isocyanate-functional prepolymers such as are disclosed, for example, in U.S. Pat. No. 4,968,542 the disclosure of which is herein incorporated by reference.

Suitable, and presently most preferred, soft resins for use in the support materials of the present invention include moisture-curing polyurethane prepolymers prepared by the reaction of a polyol with an excess of polyisocyanate. The starting materials may be from the same chemical classes as those used to form the rigid (or "hard") polyurethane casting materials well known in the art as described in U.S. Pat. Nos. 4,376,438, 4,433,680, 4,502,479, and 4,667,661. However, the isocyanate equivalent weights of the prepolymers, the NCO:OH ratio, and/or the average hydroxy equivalent weight of the polyol are modified to obtain the semi-rigid properties of the soft region.

Additionally, other active hydrogen materials may be used alone or in conjunction with polyols to produce soft resins which will be useful in this invention. Examples are primary and secondary amines, carboxylic acid and thiols. When materials such as these are used, the overall equivalent weight of the active hydrogen components should preferably be at least 400 grams and most preferably at least 1000 grams.

Suitable isocyanates include those disclosed above. Those which are preferred include 2,4'-diphenylmethane diisocyanate, 4,4'-diphenylmethane diisocyanate, and mixtures of these isomers together with possible small quantities of 2,2'-diphenylmethane diisocyanate (typical of commercially available diphenylmethane diisocyanate). Suitable commercially available isocyanate starting materials include "ISONATE" 2143L (Dow Chemical Co.), "MONDUR" MRS (Mobay Chem. Co., Pittsburg, Pa.), and "PAPI" (Dow Chemical Co.).

The degree of rigidity and resiliency in the cured support device is generally affected by the average hydroxy equivalent weight of the polyol or polyol blend. The choice of hydroxy equivalent weight is also dependent upon the molecular structure and type of the isocyanate as is well known.

Suitable polyols for use in the prepolymer resin system include polyalkylene ethers derived from the condensation of alkylene oxides (such as those available from Arco Chemical under the tradename "ARCOL PPG," and from BASF Wyandotte under the tradename "PLURACOL"), polytetramethylene ether glycols (such as "POLYMEG" from the Quaker Oats Co.), polycaprolactone polyols, and polyester polyols (hydroxyl-terminated polyesters obtained from esterification of dicarboxylic acids and diols) such as the "RUCOFLEX" polyols available from Ruco division, Hooker Chemicals Co.). In general, by using higher molecular weight polyols, the rigidity of the cured resin can be decreased.

An especially preferred resin for use in the edge region of the support materials of the invention uses an isocyanate known as "ISONATE" 21431, available from Dow Chemical (a mixture of isocyanate compounds containing about 73% by weight of diphenylmethane diisocyanate) and a mixture of polypropylene oxide polyols available from Arco Chemical as ARCOL LHT-28 and PPG 425. To prolong the shelf-life of the materials, it is preferred to include about 0.02–0.1 percent by weight of benzoyl chloride and/or other suitable stabilizer (e.g., an antioxidant such as butylated hydroxy toluene at a level of about 0.05 to 0.25 weight percent).

The isocyanates and the polyols are reacted with one another under conventional polyurethane reaction conditions known to those skilled in the art. The NCO:OH ratio of the reactants is in the range of about 1.5:1 to 7:1 and preferably between 2.5:1 and 4.5:1.

In general, the softness of a resin may be affected by adjusting the "functionality" of the reactants. As the functionality increases, e.g., as the relative amount of polyfunctional material compared to di-functional material is increased, the softness will decrease. However, the elasticity or resilience of the material may increase somewhat. Also in general, the softness of a resin may be affected by adjusting the "equivalent weight" of the reactants for a given NCO:OH ratio. As the equivalent weight increases, e.g., as the equivalent weight of polyol is increased, the softness will increase.

To form a presently preferred soft resin having an NCO:OH ratio between 2.5:1 and 4.5:1, the theoretical isocyanate equivalent weight of the prepolymer preferably is greater than about 400 grams, more preferably greater than about 500 grams, and most preferably greater than about 1000 grams. Preferably the theoretical polyol equivalent weight of the prepolymer is greater than about 400 grams, more preferably greater than about 500 grams, and most preferably greater than about 1000 grams. Of course these weights might be different were the resin to contain an adjuvent such as a plasticizer (which, in general, will reduce the rigidity of the cured resin) or utilize a different NCO:OH ratio or average functionality of reactants.

The reactivity of the one or more resins once they are exposed to the water curing agent can be controlled by the use of a suitable amount of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl) ethoxy]ethyl]-morpholine ("MEMPE") prepared as described in U.S. Pat. No. 4,705,840 and 2,2' dimorpholinodiethyl ether ("DMDEE") prepared as described in U.S. Pat. No. 4,433,680, the disclosures of which are incorporated by reference, at a concentration of about 0.05 to about 5 percent by weight (based on total resin weight). To produce the cured support devices of the present invention, a cure time of about 2.5 to 18 minutes following exposure to the curing agent, e.g., dipping in water, is preferred. More preferably, the cure time is between about 3 and 10 minutes, and most preferably between about 3 and 5 minutes.

In general, foaming of the resin should be minimized in the hard region of the casting tape since it may adversely impact the surface smoothness of the cast and may decrease the cast's overall strength. Foaming may occur, for example, when carbon dioxide is released as a result of water reacting with an isocyanate group. One way to minimize foaming is to reduce the concentration of isocyanate groups in the prepolymer. However, to have reactivity, workability, and ultimate strength, an adequate concentration of isocyanate groups is necessary. Although foaming is less at low resin contents (e.g., at low resin coating weights), adequate resin content is required for desirable cast characteristics such as strength and resistance to peeling. A satisfactory method of minimizing foaming is to add a foam suppresser such as silicone Antifoam A (Dow Corning), or Anti-foam 1400 silicone fluid (Dow Corning) to the resin. It is especially preferred to use a silicone liquid such as Dow Corning Anti-foam 1400 at a concentration of about 0.05 to 1.0 percent by weight. Water-curable resins containing a stable dispersion of hydrophobic polymeric particles, such as disclosed in European Published Patent Application EPO 0 407 056, may also be used to reduce foaming.

If desired, foaming of the resin may be used to advantage in the soft region of the casting tape. For example, foaming may have a desired effect of lowering the rigidity of the edge region of the casting tape. The foaming may be adjusted by coating at least one edge region of the tape with a resin that does not have an anti-foam agent (thereby allowing foaming to occur naturally during cure of the resin) or by coating the region with a resin that contains a foaming agent such as GR-5M triton surfactant from Union Carbide.

Lubricants are preferably added to the resin or resins, e.g., as described in U.S. Pat. Nos. 4,667,661 and 4,794,937, such that the casting materials exhibit reduced tack prior to and during cure and yet form a cast with acceptable strength and lamination strength. This is especially true for the soft resins used in the edge region. These resins tend to be even more sticky than those used to form rigid casts. Suitable lubricants include: hydrophilic groups which are covalently bond to the resin system; additives which are incompatible with the curable resin including surfactants, polymers comprised of a plurality of hydrophilic groups, and polysiloxanes; and combinations of the above. If desired, the lubricant may be used in conjunction with a separate fugitive liner such as are disclosed in U.S. patent application Ser. No. 08/404,242.

The preferred method of detackifying the polyurethane prepolymer resin systems involves the addition of a lubricant, especially a surfactant, to the system. The preferred surfactants are block copolymers of propylene oxide and ethylene oxide or polyethylene oxides which are solids at 23° C. in an amount ranging from 3 to 6 percent by weight of the prepolymer system. Especially preferred are hydroxy functional polyethylene oxide terminated polypropylene oxides (sold under the tradename "Pluronic" by BASF Wyandotte).

Plasticizers may be added to the resin to adjust the cured resin's hardness. Suitable plasticizers are well known in the art and are preferably added to the soft resin in amounts that provide the desired level of softness to the cured article. Preferably, the plasticizer does not adversely affect the shelf stability of the uncured casting tape or otherwise negatively impact the physical or toxicological properties of the material. Suitable plasticizers include materials such as Butyl Benzolphalate, Sanicizer 160, from Monsanto Chemical Co.

Presently preferred resins are the aforementioned urethane resins formed by the reaction of a polyisocyanate and a polyol. Other water-curable resins known in the art (optionally combined with moisture sensitive catalysts) may be suitable, including polyurethanes, cyanoacrylate esters, epoxy resins and prepolymers terminated at their ends with trialkoxy- or trihalo-silane groups.

Resin systems other that those which are water-curable may be used, although the use of water to activate the hardening of an orthopedic casting tape is most convenient, safe and familiar to orthopedic surgeons and medical casting personnel. Preferred resins are not appreciably dispersible in water. Suitable water-activated and alternative curing resins include moisture-curing polyurea prepolymers, silane, siloxane, epoxy, acrylate, polysulfide and polyester functional materials. Light-curing materials such as certain active olefins, e.g., acrylates and pendant vinyls, are also candidates.

Suitable resins include those disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol). The resin may be hardened upon wetting with solutions of a tertiary amine and an organic peroxide. Alternatively, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system).

Also included as resins in this invention are water curable alkoxy silane terminated oligomers such as are disclosed in U.S. Pat. No. 5,423,735 which is herein incorporated by reference.

Also included as resins in this invention are water reactive liquid organometallic compounds such as are disclosed in U.S. patent application Ser. Nos. 08/008,678 and 08/008,743 (now U.S. Pat. Nos. 5,364,693, and 5,346,939) which are herein incorporated by reference. These resins generally consist of a water-reactive liquid organometallic compound and an organic polymer.

It is desirable that the rheology of the curable resin be adjusted so that the resin can be easily coated on the backing at the desired coating weight, yet does not "pool" during storage. More preferably, when two different resins are employed, it is desirable that the different resins resist undesirable migration that would compromise the unique cured physical properties of the different regions of the casting tape. This may be accomplished, for example, by providing one or more of the resins in a form that resists migration.

The flexible sheet material used in the support material of the present invention is preferably porous such that the sheet is at least partially impregnated with the resin. A porous sheet material also facilitates circulation of air through the cured device and evaporation of moisture from beneath the device. This contributes to the patient's comfort and to the maintenance of healthy skin under the device.

Examples of suitable flexible sheet materials include woven or knit fabrics comprised of natural or synthetic fibers such as polyamide, polyester, cotton, rayon, polyolefin, etc. Preferred sheet materials are extensible knit fabrics of fiberglass or polyester. Suitable fiberglass fabrics are disclosed in U.S. Pat. Nos. 4,502,479; 4,609,578; 4,668, 563; and 5,014,403; and in U.S. patent application Ser. Nos. 07/976,402 and 08/008,751 (now U.S. Pat. Nos. 5,353,486; and 5,405,643) which are herein incorporated by reference. Particularly preferred sheets of this type are extensible, heat-set fabrics as disclosed in U.S. Pat. No. 4,609,578 (Reed) which is herein incorporated by reference.

Preferred sheet materials used in the support material are generally long, narrow fabric strips (tapes) wound in rolls of various widths, e.g., from about 5 cm to about 15 cm wide. The fabric is impregnated with the curable resin material in an amount of about 30 to 90 percent by weight of the support material, and in the preferred embodiment, employing a fiberglass fabric, of from 40 to 60 percent by weight of the impregnated support material. The term "impregnate" is used to describe the condition in which the resin is thoroughly intermingled with and in surrounding relation to the threads or fibers of the fabric and does not necessarily indicate that the resin is to any extent absorbed by the fibers themselves. Generally, the resin solution will flow into the capillary spaces between contiguous filaments of the fabric and will become bonded to the fabric upon curing.

The amount of resinous component applied to the fabric must be sufficient for the formation of a interlayer laminate bond, but preferably not so much as to occlude the porosity. Excessive resinous component may also cause the support material to be messy to handle due to stickiness or dripping of the resin.

If desired, the fabric may be knit using two different types of wale yarns. A first type of yarn (e.g., fiberglass) may be used to form a center region of the fabric while a second, softer type of yarn (e.g., polyester) may be used to form at least one edge region of the fabric. The softer edge yarns will provide a lower modulus cured edge region relative to the higher modulus center region. The fabric may alternatively be knit using a single type of yarn or treated in a manner such that a first region of the fabric absorbs more or less of the curable resin. For example, the capacity of a wale yarn to absorb resin may be adjusted by increasing or decreasing the number of fibers in the wale yarn. In this manner, more or less resin can be directed to a particular wale, resulting in differential hardness of the cured fabric.

The resin coated fabric strips in roll form are preferably wound on a plastic core and sealed within a moisture and oxygen impermeable package. In the case of moisture-curing resins, the package is opened immediately before use and the roll is fully immersed in tap water for about 5 to 30 seconds. This is sufficient time for water to seep into the porous material and displace air. As long as the resin content is not so high as to cause the openings in the fabric to be filled with resin, more than enough water is absorbed by the roll in this manner. The roll may be squeezed underwater to replace entrapped air with water. When the roll is unwound during wrapping of the material, the excess moisture coats freshly exposed resin surfaces insuring thorough wetting and rapid curing of the material. An alternate method comprises wrapping the material without dipping and then allowing atmospheric moisture or water provided by spraying or by application of a wet towel to cure the prepolymer.

Prior to applying the support material, protective padding is optionally positioned about the limb of the patient. The padding may take the form of a tubular stockinet or some other convenient form, such as for example, an elongated strip or bandage which may be wrapped about the body member.

Figure 4:
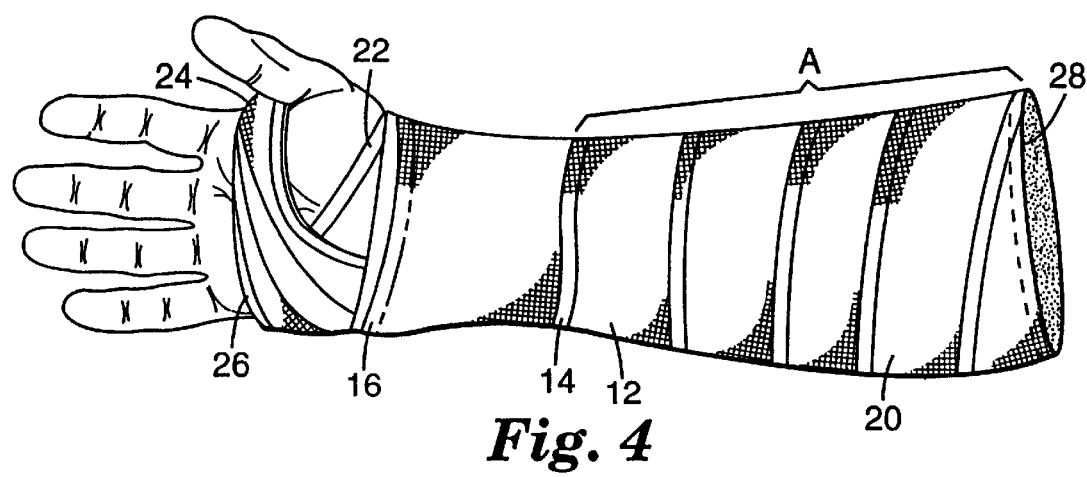
FIG. 4 shows a human arm wrapped with the casting tape of the present invention.

With the padding in proper position, the moistened support material is wrapped about the limb and over the protective padding in a manner similar to the application of a standard casting material. The material is also shaped in a manner similar to the shaping of a rigid synthetic or plaster cast. When wound in a spiral pattern, as shown in portion A of FIG. 4, the edge regions overlap the center region of one or more adjacent layers. Consequently, the strength of the cast is not significantly compromised in this area. Preferably, however, the edge region is overlapped against the edge region of one or more adjacent layers near the edge of the cast to form a soft edge of the cured cast.

Eight or fewer layers of the support material should generally be sufficient to form a cured device providing adequate support and/or immobilization for most applications.

The cured support devices of the present invention are characterized by their flexible and resilient edges as compared to conventional rigid casts formed of synthetic resins.

In an alternative embodiment, the support material comprises an extruded sheet material of either a thermoplastic material or a viscous curable material. Suitable extruded sheet materials are disclosed in copending U.S. patent application Ser. Nos. 08/048,891; 08/391,1 1 1; 08/391,712; and 08/449,505, which are herein incorporated by reference.

In accordance with the present invention, the extruded sheet is formed using at least two strips of extruded material having differential cured or hardened properties.

The extrusion process may produce a product with any number of configurations including random forms such as found in NOMAD matting (available from 3M and described in U.S. Pat. No. 4,351,683). Alternatively, the apertured sheet may be extruded as a continuous non-apertured film which is then punched or drilled to form an apertured sheet. Presently preferred extruded apertured sheets are formed by the "Z-web" process disclosed in U.S. Pat. Nos. B1 4,631,215 and B1 4,634,485 or by the "Spiral" process disclosed in U.S. Pat. No. 4,384,022. Another suitable process, the "Conwed" process, provides an extruded netting having two sets of strands which cross each other at substantially a right angle and which may be molecularly oriented (described, for example, in U.S. Pat. Nos. 2,919,467, 3,252,181, and 4,152,479). The aforementioned patents (U.S. Pat. Nos. 2,919,467, 3,252,181, 4,152,479, 4,351,683, 4,631,215, 4,634,485, and 4,384,022) are herein incorporated by reference for their description and teaching of their respective processes.

Figure 6:
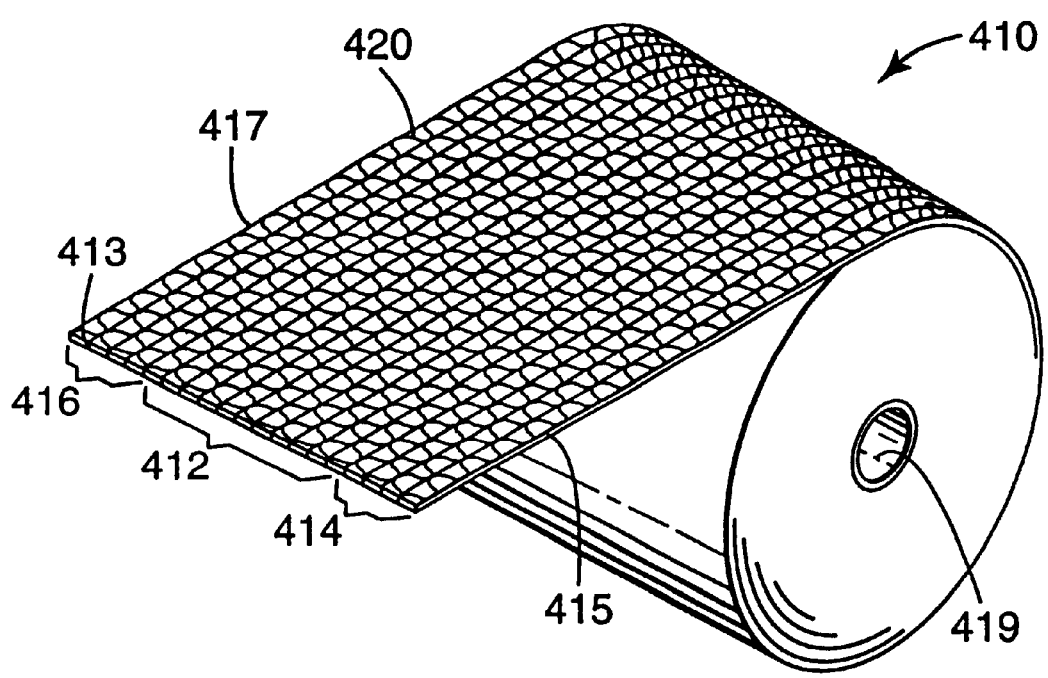
FIG. 6 shows a partially unwound roll of an extruded casting article having two soft regions along each edge of the casting tape.

The Z-web process is presently most preferred since it is capable of producing a wide variety of webs having varying density of apertures and thickness and is relatively easy to set up and maintain. The Z-web process works primarily due to differential pressure drops across the die face orifices which results in differential extrudate mass flow rates which create the "zig-zag" or Z-web pattern. A typical web pattern is illustrated in FIG. 6. Articles formed by the Z-web process are manufactured according to the following procedures:

(1) extruding at a first rate a first filament-forming extrudable plastic mass to form a plurality of straight spaced parallel elements;

(2) extruding (at a second rate faster than the first extrusion rate and between adjacent spaced, continuous parallel elements) a second filament-forming extrudable plastic mass which is preferably thinner than it is wide to provide a cross-section with an aspect ratio of preferably at least about two, with the undulatable element being positioned with each opposite face of its wide dimension facing one of the straight continuous parallel elements and wherein the plastic masses have a tacky first state which permits the elements to bond to one another at points of mutual contact and a second physical state in which the elements have sufficient structural integrity to maintain their extruded bonded shape and preferably in which latter state subsequent bonding resulting in web deformation and aperture closure will not occur;

(3) while the elements are sufficiently tacky to cause bonding therebetween at points of contact, causing the undulatable element to undulate in its thin dimension by permitting contact between a parallel element on one side of the undulatable element while maintaining the other adjacent parallel element in sufficiently close proximity to permit subsequent contact between it and the undulating undulatable element and to permit repetition of such undulation and subsequent contact, thereby providing an article having an undulated element with apexes aligned on opposed sides wherein the apexes on one side of the undulated element are bonded to one of the parallel elements and the apexes on the other side of the undulated element are bonded to the other adjacent parallel element; and (4) changing or permitting the change of the plastic masses to the second physical state.

Webs made by the Z-web process may aesthetically resemble a knitted web. In order to ensure adequate breathability in a tape form, webs made by the Z-web process preferably have between 7.75 and 77.50 apertures per cm$^2$, more preferably between 15.50 and 62.00 apertures per cm$^2$, and most preferably between 23.25 and 38.75 apertures per cm$^2$. As used herein, a cast which has sufficient porosity to allow moisture vapors produced by the skin to freely escape through the cast is said to be "breathable" or to "breathe." For the Z-web configuration an aperture is defined as a triangular or sinusoidal type aperture as shown in FIG. 6. Preferred Z-web casts are as breathable as typical fiberglass casting tapes such as SCOTCHCAST PLUS (available from 3M Co., St. Paul, Minn.). Moisture vapor transmission and air flow through a casting material may be tested as described in the aforementioned patent applications. Preferably, the casts of the present invention have comparable air flow and moisture vapor transmission to plaster of Paris materials or traditional fiberglass casting materials.

The Spiral process is also preferred since it is capable of producing a wide variety of webs having varying density of apertures and thickness and is relatively easy to set up and maintain. The Spiral process also works primarily due to differential pressure drops across the die face orifices which results in differential extrudate mass flow rates which create the spiral pattern. In contrast to the Z-web process, the Spiral process utilizes a die which comprises one or more inner orifices and a plurality of outer orifices (at least three) which surround each inner orifice. The geometry of the die produces a web which comprises one or more filament bundles having a spiral shaped inner extrudate surrounded by a plurality of straight, parallel outer "cage" filaments. The sizes and cross-sectional shapes of the orifices determine the size and shape of the filaments extruded through them. For a given spacing between the inner orifice and the outer orifices, the pitch of the spiral core filament is determined by the relative material flow through the inner and outer holes. That is, the pitch reduces as the velocity differential increases.

The Nomad process is described in U.S. Pat. No. 4,351,683. This process is capable of forming a resilient open fibrous web of inter-engaged continuous kinky filaments. The method involves extruding a bundle of filaments of a material having a tacky first state which permits the elements to bond to one another at points of mutual contact and a second physical state in which the elements have sufficient structural integrity to maintain their extruded bonded shape, and in which latter state subsequent bonding will preferably no longer occur, aligning the bundles so the filaments fall upon a contact surface, and advancing the resulting web at a slower rate than the rate of extrusion.

Webs made by the Spiral or Nomad processes should preferably have a sufficient number of apertures to provide adequate breathability, preferably as much breathability as provided by the Z-web materials. However, due to the geometry of the Spiral webs, and the random nature of the Nomad webs, it is difficult to specifically count the number of apertures per unit area. An alternative method of quantifying the breathability of these webs is to calculate the aperture volume of the web. Suitable webs made by the Spiral or Nomad processes have a sufficient percent aperture volume to provide adequate breathability. More preferred webs have as much breathability as provided by the Z-web materials or typical fiberglass casting tapes such as SCOTCHCAST PLUS from 3M. A web's "aperture volume," as used herein, is determined by first weighing a known volume of web to determine web density. The volume of extrudate in that area of web is then calculated by dividing the measured web weight by the extrudate density. The volume of extrudate divided by the web volume, calculated as the area of the web times its average thickness, gives the fraction extrudate in the mat, which subtracted from one and multiplied by 100 gives the percent aperture volume. The web thickness is determined using an Ames (Waltham, Mass.) model 2 thickness gauge.

In order to ensure good conformability, moldability, and handling, yet provide adequate strength the tape thickness should be between 0.25 and 8.0 mm, more preferably between 0.5 and 4.0 mm, most preferably between 0.75 and 2.00 mm. An orthopedic splint may be formed from multiple layers of thinner tape or may be extruded directly in a thicker form. If extruded directly the material could have from 1.55 to 46.5 apertures per cm$^2$ (or its equivalent aperture volume) and have a thickness of between 2.54 and 12.70 mm, more preferably between 5.08 and 8.89 mm.

In one embodiment of the present invention an extruded casting tape or splint is provided as a thermoplastic apertured web. This embodiment offers an environmentally friendly and hazard-free alternative in casting. The thermoplastic casting tape preferably includes an extruded apertured web comprising at least two different strips of thermoplastic polymers with controlled amorphous phase rheology. A first polymer composition forms a soft casting material when cooled to room temperature, the second polymer composition forms a hard casting material when cooled to room temperature. Preferably, the soft casting material forms at least one edge of the casting tape.

Suitable thermoplastic polymers for use in the present invention are those polymers which soften or melt at temperatures which can comfortably be withstood by the patient and/or technician during the cast's application. This temperature is believed to be less than about 90° C., preferably less than about 75° C., although somewhat higher temperatures may be acceptable (especially in situations where direct contact of the casting material and skin are avoided). Suitable thermoplastic polymers include polyurethanes (especially polyurethanes based on semi-crystalline polyester polyols), polyethylene, ethylene vinyl acetate, cis and trans polyisoprene, polyesters such as polycaprolactone and the like. The currently preferred thermoplastic polymers for use in the present invention are semi-crystalline polyesters. Polycaprolactone and blends of polycaprolactone are particularly preferred.

In a second embodiment of the present invention an extruded casting tape or splint is provided as a viscous curable resin apertured sheet. This embodiment offers a product which will have very good conformability and should be inexpensive to manufacture. Casting materials of this embodiment preferably do not require cumbersome disposable liners or fabric backings and will provide a moldable slippery material which is easy to apply.

The viscous curable resin casting tape preferably includes an extruded apertured web comprising a curable resin, preferably water curable, having a sufficient viscosity or yield stress to resist flow at ambient temperature for extended periods of time. The extruded viscous curable resin casting tape preferably contains no backing (or only a light weight backing). Therefore, the tape's conformability and handling will be principally determined by the viscosity of the curable resin component. By adjusting the rheological properties of the resin a product with superior conformability and moldability which is also much less expensive to manufacture than current synthetic casting tapes will be possible.

Curing of the resin may be initiated by exposure to water or by a conventional free radical mechanism. Water curable resins are preferred since this is most convenient and familiar to the clinician. Therefore, while the following discussion focuses on water curable resins, it is understood that materials cured by alternative means are suitable.

A significant technical feature of the present invention is the development of a curable resin system, preferably water curable, which can be extruded through an appropriate die and then can be subsequently gelled to a viscous or high yield stress state. The terms "gel" or "gelled," as used herein, describes materials which have or develop a high enough yield stress to resist flow at ambient temperature for extended periods of time. Preferred materials are gelled to a point where the web integrity is sufficient to resist a tension of at least 0.0175 N/mm width, more preferably at least 0.0875 N/mm width and most preferably over 0.175 N/mm width without breaking and without collapse of a substantial portion of the extruded apertures or voids. Preferred materials have a storage- or elastic-modulus, G', of at least 0.1 dyne/cm$^2$ at 0.1 rad/sec and 1 dyne/cm$^2$ at 1.0 rad/sec. More preferably G' is at least 1 dyne/cm$^2$ at 0.1 rad/sec and 10 dyne/cm$^2$ at 1.0 rad/sec as determined using a parallel plate rheometer such as a Rheometrics Dynamic Analyzer model RDA-II. For ambient temperature curable resins G' is determined at 25° C. under an inert atmosphere. For thermoplastic resins G' is determined at 5 degrees above the melt temperature used in application of the casting material.

A "gelled" resin system may be achieved by forming a composite of inorganic and organic fillers and a resin. Suitable concentrations of filler in the resin (i.e., "filler loading") will vary depending on the bulk density of the filler, and the specific gravity of the filler and particular resin employed. A suitable filler loading is determined by selecting a level which is sufficiently high to ensure adequate composite strength and good web integrity but not so high that the composite easily fractures or crumbles or is difficult to extrude. Preferably, the filler loading is also high enough to allow the clinician to apply the material to the patient's limb without requiring gloves.

The curable resin used in the casting material of this embodiment of the present invention is preferably any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. In a short time following completion of cast application, it should become rigid and strong enough to support loads and stresses to which the cast is subjected by the activities of the wearer. In the case of the soft region, it should become at least semi-rigid. Thus, the material must undergo a change of state from a viscoelastic condition (e.g., a material having a high enough yield stress to resist flow at ambient temperature for extended periods of time) to a solid condition in a matter of minutes. The preferred resins are those cured with water. Presently preferred are urethane resins cured by the reaction of a polyisocyanate and a polyol such as are described herein.

The materials and compositions of the present invention may be fabricated into a variety of configurations including splints, tapes, protective pads, and preformed shapes.

As previously mentioned, preferred sheet materials used in the support material are generally long, narrow fabric strips (tapes) formed in rolls of various widths, e.g., from about 5 cm to about 15 cm wide. Likewise, the support devices are generally long, narrow tapes formed in rolls of various widths. Suitable cured support articles have a center region and at least one edge region having differential hardness. Preferred cured support articles have two soft edge regions.

For use as an orthopedic casting bandage, the edge region is preferably wide enough that the cured casting bandage provides a "soft" edge that does not abrade or cut the wearer's skin or otherwise hurt the wearer. For a typical 10 cm wide casting bandage, the edge region is preferably at least 0.5 cm wide, more preferably at least 1 cm wide, and most preferably at least 1.5 cm wide. The edge region is preferably narrow enough that the cured casting bandage provides a provides a rigid support device that can support the weight normally carried by the limb around which the support device is wrapped. For a typical 10 cm wide casting bandage, the edge region is preferably less than 4 cm wide, more preferably less than 3 cm wide, and most preferably less than 2 cm wide.

Typical commercially available synthetic orthopedic casting materials comprise a knit fiberglass fabric impregnated with a polyisocyanate prepolymer resin. Typical knit fiberglass fabrics comprise between about 4 and 7 wales per cm width. Consequently, a 10 cm width casting bandage typically would comprise between about 40 and 70 wales. For a 10 cm wide fiberglass casting bandage, the edge region preferably involves at least 2 wales, more preferably at least 5 wales, and most preferably at least 7 wales. Additionally, for such a casting bandage, the edge region preferably involves less than 20 wales, more preferably less than 15 wales, and most preferably less than 10 wales. By "involvement" of the wales is meant that the wales are coated with a particular resin that provides a soft region or the wales are formed using a particular yarn that provides a soft region or by a combination of both mechanisms.

The present invention relates to an article which is suitable for forming an orthopedic splint around a portion of an animal body part. When fabricated as a splint, the material may be provided as a precut slab (e.g., as illustrated in FIGS. 5a–d) or a continuous length form. The soft edge region may run the length of the splint or be located at the ends of the splint or both. For example, a rectangular splint material preferably comprises a soft edge around all four edges of the splint and near any optional appendage holes, e.g., thumb holes. Furthermore, the splint may be provided with or without a covering and/or padding. Suitable coverings and paddings for use in this invention are discussed in U.S. Pat. Nos. 5,027,803 and 4,899,738 which are herein incorporated by reference. The splint may have a padding material on one or both sides.

According to a present preferred embodiment of the invention, a unitary blank is provided which comprises a pliant, preferably extensible, and highly conformable substrate. The blank is dimensioned in a first direction sufficient to extend the length of the body part and is dimensioned in a second direction sufficient to extend partially, but preferably not completely, around the circumference of the body part. In this regard, the blank is dimensioned in the second direction so as to envelop the body part to the extent that is needed to support and immobilize the body part, while still accommodating for the swelling which generally occurs as a result of a fresh fracture or soft tissue injury.

The blank preferably comprises a backing and a water-curable, isocyanate functional, prepolymer resin impregnated into the backing.

Figure 5A:
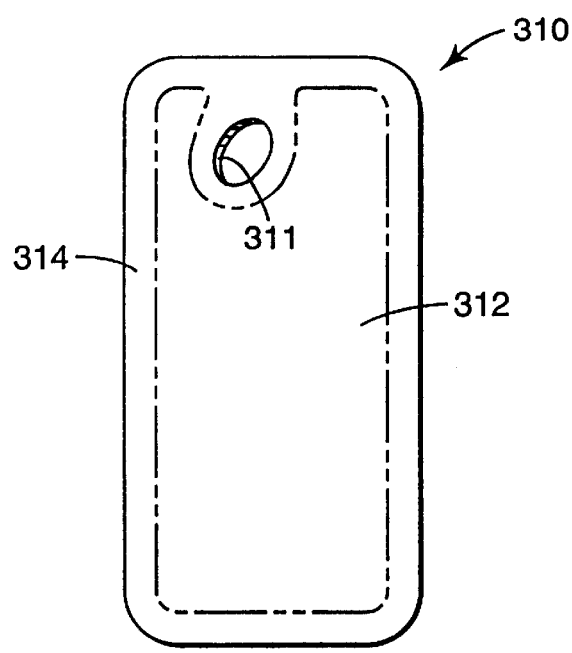
FIG. 5a shows a splint article having a soft region along the edge of the splint and around a thumb hole.
Figure 5B:
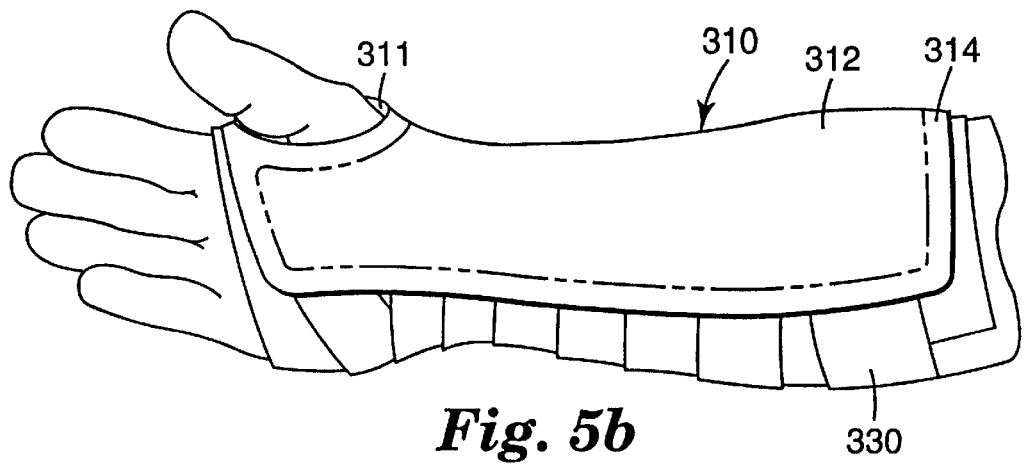
FIGS. 5b and 5c show the splint article of FIG. 5a adapted to a human arm.
Figure 5C:
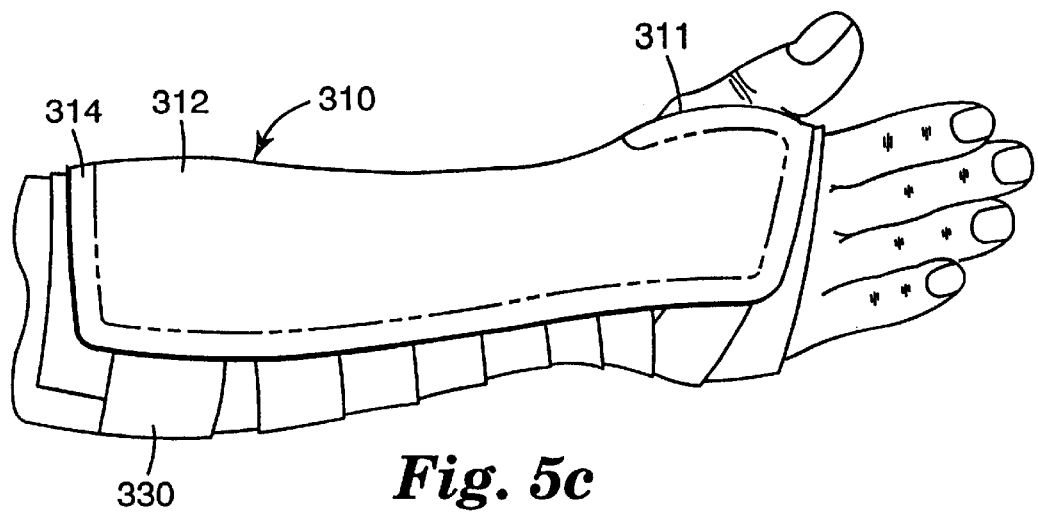
Figure 5D:
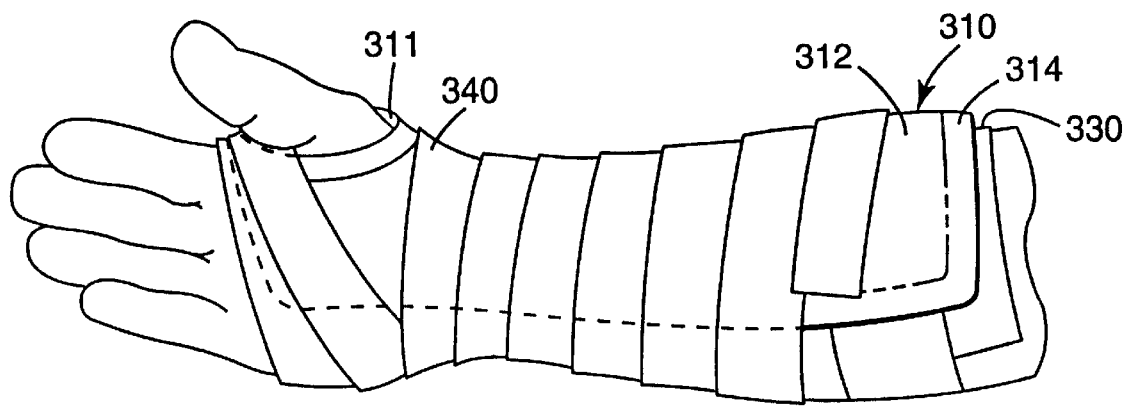
FIG. 5d shows an overlay bandage wrapped around a human arm and over the splint article of FIGS. 5b and 5c.

FIG. 5a is a plan view of a preferred forearm embodiment of the orthopedic splinting article of the present invention prior to application; FIG. 5b is a perspective view of one side of the orthopedic splinting article of FIG. 5a which has been trimmed to fit and formed into a forearm splint; FIG. 5c is a perspective view of the opposite side of the orthopedic splinting article shown in FIG. 5b; and FIG. 5d is a perspective view of the embodiment of FIG. 5b additionally showing a bandage which may be optionally wrapped around the splinting article in order to provide better conformability and attachment of the splinting article to the forearm.

Referring now to FIG. 5a, there is shown in plan view a preferred forearm orthopedic splinting article 310 of the present invention in the form of a unitary blank. The article or blank 310 is generally comprised of a pliant sheet and preferably has a thumbhole 311 formed therein to facilitate application of the article 310 around a wearer's forearm as shown in FIGS. 5b–d. Article 310 of FIG. 5a may be initially configured as a rectangle, and then be trimmed to custom fit the patient as shown in FIGS. 5b and 5c. In this regard, the physical characteristics of the sheet material preferably allow for easy trimming.

The sheet of article 310 preferably includes a suitable backing material and a curable resin associated with the backing. Suitable backing materials include knit, woven or nonwoven fabric materials, open-celled foam sheets, and the like.

For the forearm splint embodiment of FIGS. 5a–d, a sheet approximately 17.8 cm wide, 30.5 cm long, and 1.3 cm thick is presently preferred. For the lower leg embodiment, a foam sheet approximately 25.4 cm wide, 96 cm long, and about 1.3 cm thick is presently preferred. However, it will be appreciated that the exact dimensions employed may vary according to the respective limb sizes of the individual to be treated.

The orthopedic splinting article 310 is sized according to the forearm of the patient, and may be trimmed prior to application in order to provide a more exact fit. The thumbhole 311 may be formed by either punching or cutting out a corresponding portion of article 310.

Before actually applying article 310 to the forearm, a flexible stockinet or cast padding 330 is preferably placed around the patient's forearm so as to prevent undesirable adhesion or contact between the splint and forearm of the patient. For example, a tubular padding material, such as one side lofted tubular fabric made on an athletic sock machine available from Broadway Knitting Mills, 2152 Sacramento Street, Los Angeles, Calif. 90021, may be used for this purpose.

The splint of FIGS. 5a–d is formed by first activating the resin of article 310 of FIG. 5a with water. Next, the left or right hand thumb of the patient is passed through aperture 311, and the long edge of the rectangular article is longitudinally aligned with the patient's forearm. The article is then circumferentially molded or positioned around the forearm to the position shown in FIGS. 5b and 5c. In this regard, the resin impregnated sheet has excellent compression moldability or conformability to provide a good fit around the patient's forearm.

The article 310 is sufficiently dimensioned in its longest direction to extend the length of the forearm to be immobilized by the splint. The article 310 is dimensioned in the other direction so as to accommodate swelling of the forearm. This is preferably done by configuring article 310 so that it extends partially, but not completely, around the circumference of the forearm. In this regard, in order to accommodate the swelling of the forearm, the orthopedic splint 310 preferably extends around about 40% to about 90% of the circumference of the forearm, and most preferably around about 60% to about 75% of the circumference of the forearm. Such partial enclosure allows for swelling of the injured forearm, yet provides adequate immobilization thereof to promote healing.

However, it will be appreciated that the splinting article could also be configured in the circumferential direction so as to completely surround the forearm if desired. In order to accommodate swelling in such an instance, it is important that there remain a longitudinal break in the splinting article. Thus, although not the presently preferred embodiments, the splinting article could be merely wrapped around the forearm until the longest edges come into close proximity or even meet (without sealing the edges), or alternatively, so that the longest edges actually overlap slightly, but again without sealing the edges together so that the splint could still expand to accommodate swelling. Means to prevent sealing of the edges include the use of a nonadhering layer inserted between overlapping edges.

The orthopedic splinting article 310 is preferably held in place while the resin is curing by the aid of securing means. For example, wrapping means such as a stretch bandage 340 shown in FIG. 5d may be used to secure article 310 around the forearm during curing so that the resultant orthopedic splint will conform well to the forearm. Although a right arm is shown, it will be understood that the splinting article 310 may be applied equally well to a left arm.

After application, article 310 can be easily adjusted or repositioned during curing (but prior to setting of the resin) without substantial wrinkling. Furthermore, after curing and after the splint has served its intended purpose, the splint can be removed from the patient's forearm by unwrapping the stretch bandage and then prying open the splint. The general U-shape of forearm splint 310 shown in FIGS. 5a–d has been found to exhibit excellent strength and resistance to breakage.

In summary, the orthopedic splinting article 310 of the present invention can be applied to a forearm by: (1) exposing the article to water to initiate hardening of the resin, (2) manually squeezing out excess water, (3) properly positioning the orthopedic splinting article over a stockinet or cast pad applied to the forearm, (4) trimming the orthopedic splint to the desired shape, and (5) holding the splint in place as the resin cures, e.g., by wrapping a stretch bandage or other securing means around the splint article and forearm to secure the splint in place.

The present invention also relates to an article that is suitable for forming a protective pad to be secured on a portion of the human body for protection against impact injuries which could occur during physical activities, for example, sporting or athletic events. Such a protective pad can take the form of a custom-fitted protective pad or guard, such as would be worn, for example, on a shin, thigh, foot (for example, to protect the Achilles tendon region), or arm in order to protect against injury or to protect a previous injury from further damage. The soft edge region of the protective pad may run the length of the pad or be located at the end of the pad or both. The soft edges provide protection and are flexible in order to help eliminate abrasion or irritation to skin that can be caused by hard, rigid edges, and also to help ensure a truer fit to the limb by returning to the custom-fitted shape after each muscle contraction. The protective pad generally is stored in a moisture-proof pouch until ready for application to the body part to be protected.

The protective pad may be provided as a precut slab or cut from a continuous length form and may additionally include suitable padding, coverings, added support layers, and/or means for securing the pad to the body. An additional padding layer can be useful in providing enhanced strength and/or cushioning to the protective pad, and can also serve to prevent the resin-coated backing from directly coming into contact with the user's skin or clothing. Preferred padding layer materials include nonwoven materials, such as polyesters and polyolefins, and foam materials, such as open-celled foam materials. Added coverings can enhance the appearance of the protective pad and help protect the pad from external damage and soiling. Means for securing the protective pad to the intended body part include elastic straps, belt straps, and mechanical fasteners, such as hook-and-loop fasteners. If desired, the pad itself may be constructed so that it may be securely fitted to the body part (e.g., the molding of the pad may also provides a secure fit to the body part) or the pad may be secured to a piece of clothing or other equipment and thereby secured indirectly to the body part. Preferable securing means for a protective pad, for example a leg or arm guard, include at least one durable elastic strap connected to opposite sides of the guard so that the strap can be sufficiently stretched to allow the guard to be passed over the foot or hand and then to be snugly positioned against the limb.

Multiple protective pads flexibly connected together, e.g., by elastic strap means, may provide a multiple body parts protector having at least two connected pad segments. Such protectors are useful in providing custom-fitted protective pads to multiple body parts, e.g., a baseball catcher's protector having a knee pad segment, a shin pad segment, and a foot protector. A multiple body parts protector may additionally include suitable padding, coverings, added support layers, and/or means for securing to the body.

According to a preferred embodiment of the invention, a protective pad is provided which comprises a fabric backing, preferably of approximately uniform thickness, impregnated with a hard resin in a center region and a soft resin on two opposite edge regions. Preferably, the backing is fiberglass or polyester, and the soft and hard resins are both water-curable, isocyanate functional prepolymers. If necessary, the pad can be pre-cut to a size appropriate for the limb to be protected and then exposed to water to initiate hardening of the resins. The pad is then positioned on the limb, molded to the shape of the limb to ensure a custom-fit, and held in place as the resins harden, e.g., by wrapping a stretch bandage or other securing means around the pad and limb to secure the pad in place.

In another preferred embodiment of the invention, a protective pad is constructed as a laminate from at least one layer of a backing impregnated with a hard resin and at least one layer of a backing impregnated with a soft resin. Preferably, the backings are made of fiberglass or polyester, and the soft and hard resins are both water-curable, isocyanate functional prepolymers. For example, the protective pad can be a laminate prepared by centering and sandwiching 7.6-cm wide strips of fiberglass impregnated with a hard isocyanate functional prepolymer between 12.7-cm wide strips of fiberglass impregnated with a soft isocyanate functional prepolymer. The resulting protective pad with a hard center region and soft edge regions can also comprise suitable padding to prevent the resin-impregnated backing from coming into direct contact with skin. The pad can then be pre-cut to an appropriate size, exposed to water, custom-fit to the limb, and hardened as described in the previous paragraph.

If desired the casting articles of the present invention may comprise fillers or other additives. Suitable fillers for use in the present invention include inorganic or organic, particulate or fibrous materials such as are described in U.S. patent application Ser. No. 08/463,993, the disclosure of which is herein incorporated by reference. Colored pigment fillers and blends of fillers may also be suitable.

Preferred particulate fillers have an average particle diameter less than 500 $\mu$m, more preferably less than 200 $\mu$m, and most preferably less than 120 $\mu$m. A used herein, "average particle diameter" is defined as the diameter of a sphere of the same volume as the particle.

Microfibers (such as are described in U.S. patent application Ser. Nos. 08/248,341 and 08/008,755, (now U.S. Pat. Nos. 5,474,522 and 5,354,259), the disclosure of which are herein incorporated by reference) may be added to the resin to enhance web integrity or composite strength. Preferred fibers have an average length between 25 and 5,000 $\mu$m, more preferably between 30 and 1,000 $\mu$m, and most preferably between 30 and 500 $\mu$m.

Preferred fillers and microfibers for use with water curable resins also have very low moisture content. Preferably the filler or microfiber contains less than 4% by weight absorbed water, more preferably less than 1% by weight absorbed water, and most preferably less than 0.5% by weight absorbed water. The amount of absorbed water in a filler or microfiber sample may be determined by heating the sample in an oven and measuring the sample's weight loss. For fillers or microfibers that have a high amount of moisture one may preferably dry the material prior to incorporation into the resin.

If desired, the fillers or microfibers may be surface treated using silanes, titanates, zirconates and the like to enhance resin bonding, ease of mixing, and compatibility. The surface treatment may be performed prior to incorporation of the filler or microfiber into the resin or in-situ, i.e., the surface treatment agent may be incorporated into the resin for later reaction with the filler or microfiber.

The shelf stability of the uncured casting material is an important consideration when selecting suitable ingredients. Shelf stability refers to the ability of the finished product to resist degradation during normal storage conditions. For example, for products comprising isocyanate functional polyurethane prepolymers such standard storage conditions would include storage in a moisture free environment at 25° C. The shelf stability of a casting material preferably exceeds 1 year when stored at ambient temperature (i.e., 25° C.), more preferably the shelf stability exceeds 3 years, and most preferably the shelf stability exceeds 5 years. The shelf stability of a casting material containing a curable resin may also be tested at elevated temperature (49° C.) to predict ambient temperature stability. Preferred casting materials withstand four weeks at 49° C., more preferred casting materials withstand eight weeks at 49° C., and most preferred casting materials withstand twelve weeks at 49° C.

Notably, many commercially available fillers, such as glass bubbles, are basic in nature (i.e., alkali) and may cause undesirable side-reactions in isocyanate functional polyurethane prepolymers. These side reactions may cause the resin to harden prematurely or prevent hardening at all. Preferred optional fillers are chosen so as to not upset the shelf stability of the resin material. When isocyanate functional polyurethane prepolymers systems are employed it is beneficial to ensure that the optional fillers are neither basic in nature nor contain basic impurities. Such basicity can result in side reactions (such as trimerization, allophonate formation, and biuret formation) with the isocyanate functional resin system which may limit the shelf stability of the product. Adverse effects of the basicity of the filler may be minimized by washing and/or neutralizing the filler with a suitable acid or by addition of an acid stabilizer to the resin.

Resin systems may also be colored for decorative purposes using dyes or pigments or both. Luminescent pigments may also be employed. Furthermore, one may alternatively wrap the splint or cast of the present invention with a decorative or informative sheet comprising raised lettering and/or figures which is capable of leaving impressions in the material. Furthermore, the materials of the present invention may be printed using suitable dyes or pigments by direct or indirect printing methods such as transfer printing, pigment printing, or ink jet printing.

Color conveniently may be used to deliniate the "soft region" from the "hard region." For example, the soft resin may be colored in a distinctive manner so as to be visibly different from the hard resin. Alternatively, a portion of the carrier fabric may be colored to deliniate the soft and hard regions. In either way the different colors may facilitate alignment of the soft region where desired.

A fugitive water soluble web, such as are described in U.S. patent application Ser. No. 08/404,242, the disclosure of which is herein incorporated by reference, may be employed as a liner which separates adjacent layers of the tape (e.g., when the tape is provided as a roll).

The following examples are offered to aid in understanding of the present invention and are not to be construed as limiting the scope thereof. Unless otherwise indicated, all parts and percentages are by weight.

EXAMPLES

Example 1

Casting Articles Comprising a Hard Center Region and Two Soft Edge Regions of Varying Widths A fiberglass fabric was knit according to the process described in U.S. Pat. No. 4,609,578, which is herein incorporated by reference. The fiberglass fabric was 7.938 cm wide (3⅛ inches) and had 41 wales of ECDE 75⅙ fiberglass yarn.

Sample casting tapes were made by coating the resulting fabric with two different liquid isocyanate-terminated polyurethane prepolymer resins. A first resin was a "hard resin" as described in Table 1a. A second resin was a "soft resin" as described in Table 1b.

TABLE 1a

"Hard resin"[3]

| Chemical | Equivalent weight | Parts (by weight) |
|---|---|---|
| Isonate 2143L (Dow Chemical) | 143.8 | 54.17 |
| p-Toluenesulfonyl chloride | 190.5 | 0.05 |
| Antifoam 1400 (Dow Chemical) | | 0.17 |
| Butylated hydroxytoluene ("BHT") | | 0.46 |
| NYAD-G Wollastocoat | | 5.0 |
| Pluronic F-108 (BASF) | 7250 | 3.8 |
| DMDEE[1] | 122 | 1.25 |
| Arcol PPG-2025 (Arco) | 1014.6 | 20.140 |
| Arcol LG-650 (Arco) | 85.6 | 5.87 |
| Arcol 24-32[2] (Arco) | 1737 | 8.08 |

[1]"DMDEE" = 2,2'dimorphiolinodiethyl ether.
[2]"Arcol 24-32" = Polymer filled polyol.
[3]The combined ingredients provide an NCO to OH ratio of about 4.0.

TABLE 1b

"Soft resin"[2]

| Chemical | Equivalent weight | Parts (by weight) |
|---|---|---|
| Isonate 2143L (Dow Chemical) | 143.8 | 19.98 |
| p-Toluenesulfonyl chloride | | 0.05 |
| Antifoam 1400 (Dow Chemical) | | 0.18 |
| Butylated hydroxytoluene ("BHT") | | 0.48 |
| Pluronic F-108 (BASF) | 7250 | 3.49 |
| MEMPE[1] | | 3.00 |
| Arcol LHT-28 (Arco) | 1948.1 | 29.30 |
| Arcol LHT-42 (Arco) | 1368.4 | 43.51 |

[1]"MEMPE" = Morpholinoethylmorpholinoisopropyl ether.
[2]The combined ingredients provide an NCO to OH ratio of 3.0.

The coating was performed using a three-piece slot fed die that directed the first and second resins to the center and edge regions of the casting tape, respectively. See FIGS. 8a–d. Alternatively, one may use the modified coating apparatus described in U.S. patent application Docket No. 52636USA5A "Die for Extruding Multiple Fluid Streams," (now U.S. Pat. No. 5,750,159) which is herein incorporated by reference. The coated casting tape had about 43.5 percent by weight resin.

The center longitudinally extending region of the casting tapes were coated with a first "hard" resin. The two longitudinally extending edge regions of the casting tapes were coated with a second "soft" resin in five different widths as indicated in Table 1c. Two control casting tapes were produced using the same type of fiberglass fabric but with either the soft resin (control "S") or the hard resin (control "H") coated the full width of the tape.

TABLE 1c

| Run # | Width of first edge region (cm) | Width of center region (cm) | Width of second edge region (cm) |
|---|---|---|---|
| 1 | 0.318 | 7.303 | 0.318 |
| 2 | 0.635 | 6.668 | 0.635 |
| 3 | 0.953 | 6.033 | 0.953 |
| 4 | 1.270 | 5.398 | 1.270 |
| 5 | 2.540 | 2.858 | 2.540 |
| control S | — | 7.938 | — |
| control H | — | 7.938 | — |

Ring strength was measured as described in the following procedure. A cylindrical ring comprising 6 layers of the resin-coated material was formed by taking a roll of the resin-coated material from its storage pouch and immersing the roll completely in water having a temperature of about 27° C. for about 30 seconds. The width of the ring formed was the same as the width of the resin-coated material employed, namely, 7.938 cm. The roll of resin-coated material was then removed from the water and the material was wrapped around a 5.08 cm diameter mandrel covered with a thin stockinet (such as 3M Synthetic Stockinet MS02) to form 6 complete uniform layers using a controlled wrapping tension of about 45 grams per centimeter width of material. Each cylinder was completely wound within 30 seconds after its removal from the water.

After about 20 minutes from the initial immersion in water, the cured cylinder was removed from the mandrel. Ring strength was determined 24–72 hours after initial immersion in water, i.e., those samples were allowed to cure for at least 24 hours in a controlled atmosphere of 25° C.±2° C. and 55%±5% relative humidity prior to testing.

At the appropriate time each cylinder was then placed in a fixture in a commercial testing machine, e.g., an Instron instrument, and compression loads were applied to the cylindrical ring sample along its exterior and parallel to its axis. The cylindrical ring was placed lengthwise between the two bottom bars of the fixture (the bars being 1.9 cm wide, 1.3 cm in height, and 15.2 cm long), with the bars spaced about 4 cm apart. The inside edges of the bars were machined to form a curved surface having a 0.31 cm radius. A third bar (0.63 cm wide, 2.5 cm high, and 15.2 cm long) was then centered over the top of the cylinder, also parallel to its axis. The bottom or contacting edge of the third bar was machined to form a curved surface having a 0.31 cm radius. The third bar was brought down to bear against and crush the cylinder at a speed of about 5 cm/min. The maximum peak force which was applied while crushing the cylinder was then recorded as the "ring strength," which in this particular instance is the "dry strength" (expressed in terms of force per unit length of the cylinder, i.e., newtons/cm). For each material, at least 5 samples were tested, and the average peak force applied was then calculated and reported as the dry "ring strength." The results of ring strength testing is listed in Table 1d.

TABLE 1d

| Run # | Width of each edge region (cm) | Ring strength (N/cm) | Standard Deviation (N/cm) |
|---|---|---|---|
| 1 | 0.318 | 114.2 | 3.7 |
| 2 | 0.635 | 101.9 | 8.4 |
| 3 | 0.953 | 82.0 | 6.1 |
| 4 | 1.270 | 73.0 | 6.7 |
| 5 | 2.540 | 37.3 | 1.8 |
| control S | — | 7.5 | 0.02 |
| control H | — | 103.5 | 5.4 |

The above data indicates that the ring strength is related to the amount of the soft resin at the edges. In general, the ring strength decreases with increasing width of soft edges. However, acceptable ring strength can be achieved even when both edges of the tape comprise soft resin. Additionally, it is anticipated that for a significant portion of a wrapped cast the soft region will overlap a hard region of an adjacent layer. It is believed that casts made from the above two-resin tapes, when wrapped around a limb, will provide more than adequate strength to immobilize a fracture.

Preferred casting products of the present invention have a hard center region made of a material that has a ring strength greater than 70 N/cm, more preferably greater than 80 N/cm, and most preferably greater than 100 N/cm. Preferred casting products of the present invention have an overall ring strength greater than 70 N/cm, more preferably greater than 80 N/cm, and most preferably greater than 100 N/cm.

Ring delamination was measured as described in the following procedure. A cylindrical ring comprising 6 layers of the resin-coated material was formed by taking a roll of the resin-coated material from its storage pouch and immersing the roll completely in water having a temperature of about 27° C. for about 30 seconds. The width of the ring formed was the same as the width of the resin-coated material employed, namely, 7.938 cm. The roll of resin-coated material was then removed from the water and the material was wrapped around a 5.08 cm diameter mandrel covered with a thin stockinet (such as 3M Synthetic Stockinet MS02) to form 6 complete uniform layers using a controlled wrapping tension of about 45 grams per centimeter width of material. A free tail of about 15.24 cm was kept and the balance of the roll was cut off. Each cylinder was completely wound within 30 seconds after its removal from the water.

After 15 to 20 minutes from the initial immersion in water, the cured cylinder was removed from the mandrel, and after 30 minutes from the initial immersion in water its delamination strength was determined.

A determination of delamination strength was done by placing the free tail of the cylindrical sample in the jaws of the testing machine, namely, an Instron Model 1122 machine, and by placing a spindle through the hollow core of the cylinder so that the cylinder was allowed to rotate freely about the axis of the spindle. The Instron machine was then activated to pull on the free tail of the sample as a speed of about 127 cm/min. The average force required to delaminate the wrapped layers over the first 33 centimeters of the cylinder was then recorded in terms of force per unit width of sample (newtons/cm width). For each material, at least 5 samples were tested, and the average delamination force was then calculated and reported as the "delamination strength." The results of delamination strength testing is listed in Table 1e.

TABLE 1e

| Run # | Width of each edge region (cm) | Delamination strength (N/cm) | Standard Deviation (N/cm) |
|---|---|---|---|
| 1 | 0.318 | 6.48 | 0.53 |
| 2 | 0.635 | 6.66 | 1.05 |
| 3 | 0.953 | 4.90 | 1.40 |
| 4 | 1.270 | 6.31 | 1.58 |
| 5 | 2.540 | 4.90 | 0.53 |
| control S | — | 4.03 | 0.35 |
| control H | — | 2.80[1] | 0.35 |

[1]Normally, the delamination strength for this control casting material would be approximately 7.706 N/cm.

The above data indicates that the delamination strength is related to the amount of the soft resin. In general, the delamination strength may decrease slightly with increasing width of soft edges. However, the delamination strength is still acceptable even when both edges of the tape comprise soft resin. Additionally, it is anticipated that for a significant portion of a wrapped cast the soft region will overlap a hard region of an adjacent layer. Casts made from the above tapes, when wrapped around a limb, will provide adequate lamination strength.

Preferred casting products of the present invention have an overall delamination strength greater than 4 N/cm, more preferably greater than 5 N/cm, preferably greater than 6 N/cm.

Example 2

TABER Stiffness of Various Commercially Available Casting Articles

Several commercially available casting tapes were measured as described determine their relative TABER stiffness. The stiffness values were following the procedures described in ASTM standard No. D5342-93 and using a Teledyne Taber V-5 Stiffness Tester (available from Teledyne, Tonawanda, N.Y.).

A single ply of casting material for each sample was unrolled and placed sheet of polyethylene film and allowed to cure under ambient conditions (e.g., 30–40% RH and at 21° C.) for approximately 48 hours. Once cured, the specimens were cut into rectangular samples having a width of 3.81 cm and a length of 6.985 cm using a Teledyne Taber "Triple Cut Shear" (available from Teledyne Tonawanda, N.Y.). The length side of the sample was perpendicular to the length of the casting tape, i.e., the stiffness values reflect the cross web stiffness values of the casting tapes. Three samples of each specimen were tested. The average results are listed in Table 2a.

TABLE 2a

| Run # | Product Name | TABER value (average) |
|---|---|---|
| 1 | CARA GLAS ULTRA[1] | 93 |
| 2 | DELTA-LITE CONFORM[2] | 376 |
| 3 | DELTA-LITE FLASHCAST[2,6] | 13 |
| 4 | DELTA-LITE S[2] | 176 |
| 5 | DYNACAST EXTRA (5 inch)[3] | 234 |
| 6 | DYNACAST PRO (7.5 cm)[3,6] | 13 |
| 7 | SCOTCHCAST PLUS EP[4] | 322 |
| 8 | SCOTCHCAST PLUS J[4] | 273 |
| 9 | SCOTCHCAST SOFTCAST[4,7] | 38 |
| 10 | ZIM-FLEX[5] | 152 |

[1]Available from Carapace A Lohmann Co., Tulsa, OK.
[2]Available from Johnson & Johnson, Rayham, MA.
[3]Available from Smith and Nephew, Germantown, WI.
[4]Available from 3M Company, St. Paul, MN.
[5]Available from Zimmer, Warsaw, IN.
[6]The DYNACAST-PRO and DELTA-LITE FLASHCAST casting materials are both examples of casting materials that comprise a typical "hard resin" coated on a relatively low modulus polyester based backing.
[7]The SCOTCHCAST SOFTCAST casting material is an example of a casting material that comprise a "soft resin" coated on a fiberglass backing. This material is generally described in U.S. Pat. No. 4,968,542.

The above data indicates that the overall stiffness of a casting product can be related to either the modulus of the backing fabric or the type of resin employed. Preferred casting products of the present invention have at least one soft edge region made of a material that has a TABER stiffness value between about 0.01 and 90, more preferably between 5 and 75, and most preferably between 10 and 50. Preferred casting products of the present invention have a hard center region made of a material that has a TABER stiffness value greater than 90, more preferably greater than 100, most preferably greater than 150, and optimally greater than 250.

Example 3

Edge Stiffness of Various Casting Articles

Several commercially available casting tapes and one casting tape of the present invention were measured as described below to determine their relative edge stiffness.

Edge stiffness was measured as described in the following procedure. A cylindrical ring comprising 3 layers of the resin-coated material was formed by taking a roll of the resin-coated material from its storage pouch and immersing the roll completely in water having a temperature of about 27° C. for about 30 seconds. The width of the ring formed was the same as the width of the resin-coated material employed. The roll of resin-coated material was then removed from the water and the material was wrapped around a 5.08 cm diameter mandrel covered with a thin stockinet (such as 3M Synthetic Stockinet MS02) to form 3 complete uniform layers using a controlled wrapping tension of about 45 grams per centimeter width of material. Each cylinder was completely wound within 30 seconds after its removal from the water.

After about 20 minutes from the initial immersion in water, the cured cylinder was removed from the mandrel. Edge stiffness was determined 24–72 hours after initial immersion in water, i.e., the samples were allowed to cure for at least 24 hours in a controlled atmosphere of 25° C.±2° C. and 55%±5% relative prior to testing.

Figure 7A:
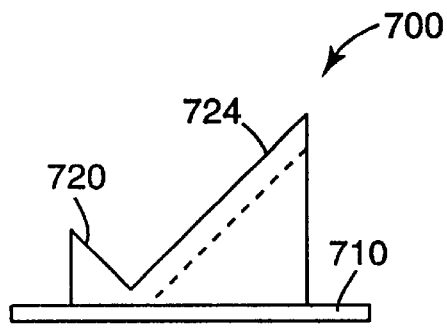
FIG. 7a illustrates a test fixture used to support a ring of casting material when measuring edge strength.
Figure 7B:
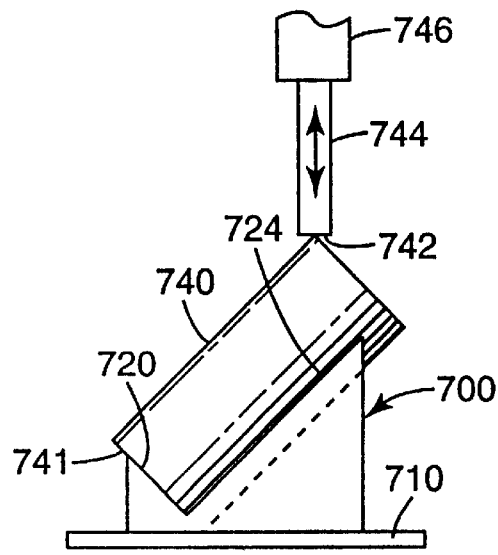
Figure 8A:
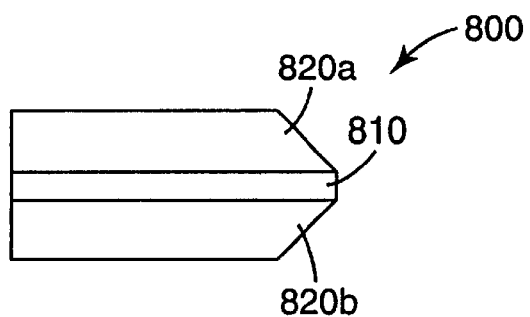
FIGS. 8a–d illustrate a slotted die used to coat two or more resins onto a backing.
Figure 8B:
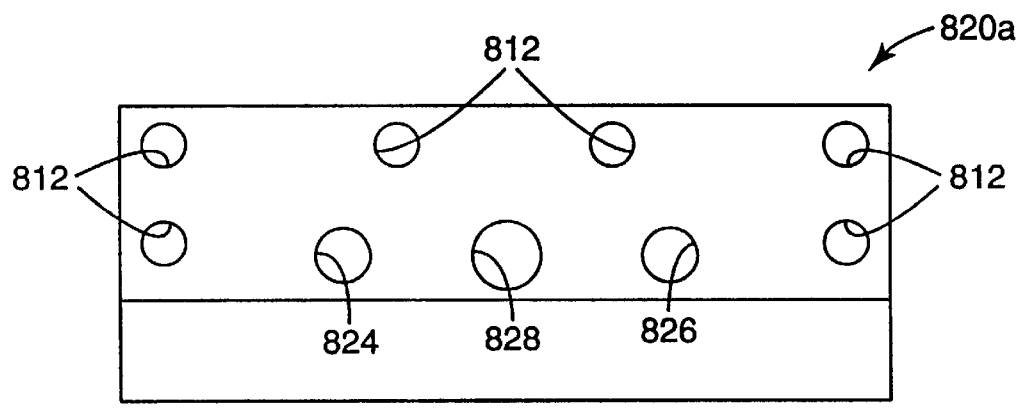
Figure 8C:
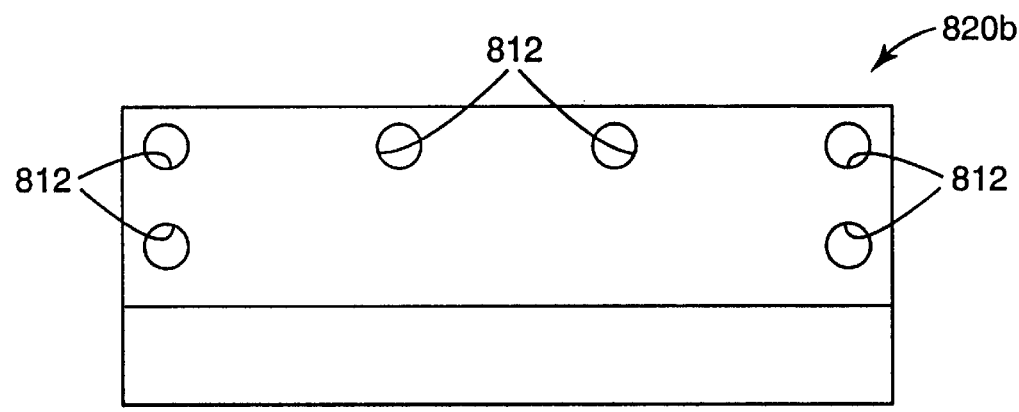
Figure 8D:
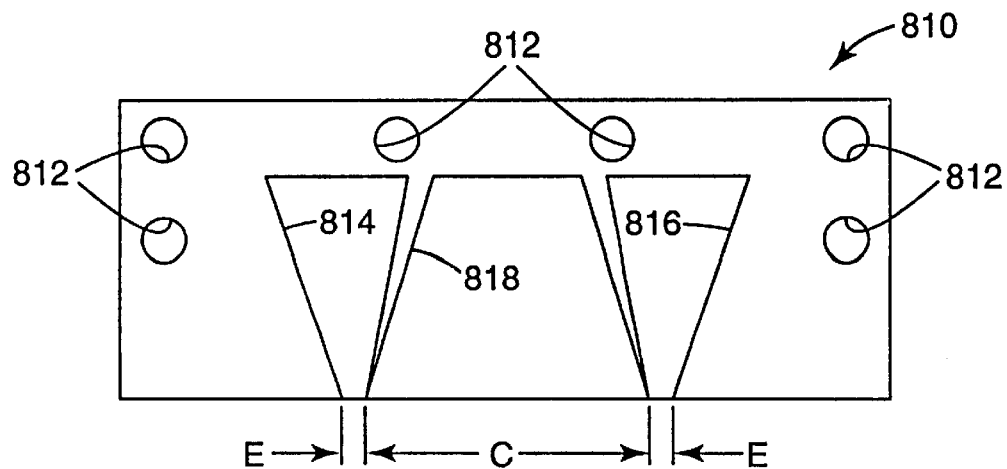

Each cylinder was placed in a fixture in a commercial testing machine, e.g., an Instron instrument. See FIGS. 7a and 7b. The fixture supported the rings at a 45 degree angle to the load plane. Compression loads were applied to the leading edge of the cylindrical ring sample using a 1.27 cm diameter probe. The position of the sample and fixture are illustrated In FIG. 7b.

The testing machine was programmed to compress the leading edge of the sample 3 mm, at which point the machine was stopped and a force reading taken. The maximum peak force which was applied while crushing the edge of the cylinder was then recorded as the "edge stiffness" (expressed in terms of force, i.e., newtons). For each material, at least 5 samples were tested, and the average peak force applied was then reported as the "edge stiffness." The results of this testing is listed in Table 3a.

TABLE 3a

| Run # | Product Name | Edge stiffness (N) |
|---|---|---|
| 1 | CARA GLAS ULTRA | 46.71 |
| 2 | CASTLIGHT 7[1] | 51.60 |
| 3 | DELTA-LITE FLASHCAST | 4.00 |
| 4 | DBLTA-LITE S | 49.82 |
| 5 | DYNACAST EXTRA (5 inch) | 48.93 |
| 6 | DYNACAST PRO (7.5 cm) | 12.46 |
| 7 | SCOTCHCAST PLUS EP | 48.04 |
| 8 | SCOTCHCAST SOFTCAST | 2.22 |
| 9 | ZIM-FLEX | 80.07 |
| 10 | Example 1, Run 3 | 4.89 |

[1]Available from Alcare Co., Japan.

The above data indicates that the edge stiffness of a casting product can be related to either the modulus of the backing fabric or the type of resin employed. Preferred casting products of the present invention have an edge stiffness value less than about 20, more preferably less than 10, and most preferably less than 5, when tested as described herein.

Example 4

Figure 9:
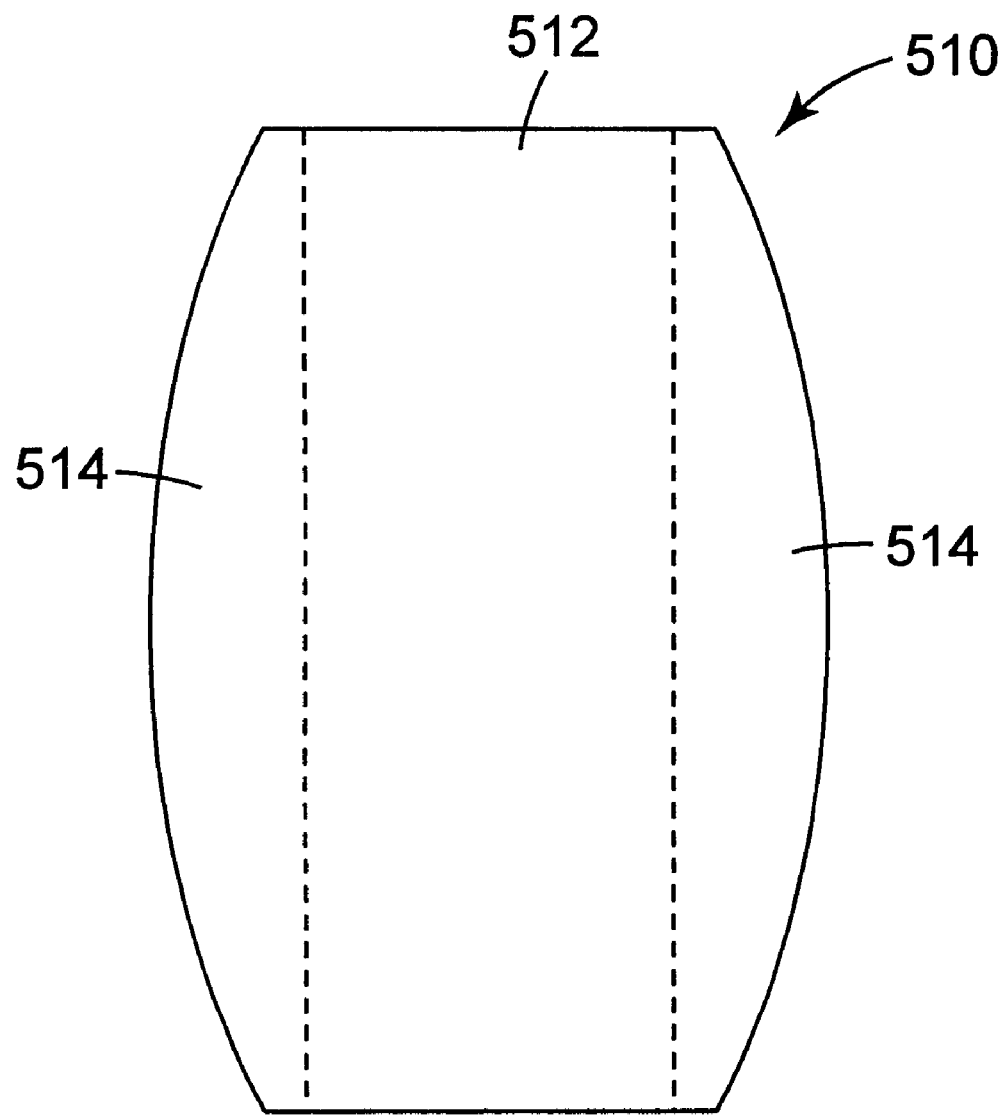
FIG. 9 shows a protective pad article having two soft edge regions and a hard center region.

Protective Pad (Shin Guard) Comprising a Hard Center Region and Two Soft Edge Regions A highly conformable, water-curable shin guard is constructed at 43° C. dew point in a dry room. Five strips (12.7 cm×22 cm) of fiberglass fabric are coated with a water-curable, isocyanate functional prepolymer resin as described in Example 1. The coating may be performed using a three-piece slot fed die that directs the "hard resin" and "soft resin" to the center region and two edge regions, respectively, of the fiberglass fabric. See FIG. 9. The coated protective pad has about 43.5 percent by weight resin in both hard and soft regions. The width of the hard center region is about 7.6 cm and the width of each soft edge region is about 2.55 cm. The five strips of the coated fiberglass fabric may be laminated together by gently applying pressure by hand and the corners of the resulting laminate pad may be trimmed with scissors to rounded shapes. The laminate may be padded by centering and pressing a strip (16 cm×25 cm) of SONTARA™ polyester nonwoven fabric (Dupont, Wilmington, Del.) to one side ("skin side") of the laminate. To the other ("top side") of the laminate is centered a strip (16 cm×25 cm) of 3M RESTON™ foam (3M Company)

with the non-adhesive side against the laminate. Additionally, a strip (16 cm×30 cm) of polyester felt (basis weight=238 g/m², Rogers Corporation, Rogers, Conn.) may be centered and adhered to the adhesive side of the foam. The resulting water-curable shin guard is sealed overnight in a moisture-impervious foil pouch. The next day, the shin guard may be removed from the pouch, wetted with water at 23° C., and applied to the shin by holding it in place with an elastic wrap. The curable shin guard is designed to be highly conformable and easily custom-fitted to the shape of the shin. The shin guard cures within about three minutes to preferably yield a custom-fitted, breathable, and protective shin guard with a hard center region and soft, flexible outer edge regions.

Example 5

Protective Pad (Shin Guard) Comprising a Hard Center Region and Two Soft Edge Regions A highly conformable, water-curable shin guard was constructed at −43° C. dew point in a dry room. Five strips (12.7 cm×22 cm) of fiberglass casting tape impregnated with a water-curable, isocyanate functional prepolymer resin ("soft resin") were cut from a roll of 3M SCOTCHCAST SOFTCAST™ casting tape (3M Company) and placed directly on top of each other. Three strips of (7.6 cm×22 cm) of fiberglass casting tape impregnated with a water-curable, isocyanate functional prepolymer resin ("hard resin") were cut from a roll of 3M SCOTCHCAST PLUS EP™ casting tape (3M Company) and placed directly on top of each other. The three strips of 3M SCOTCHCAST PLUS™ casting tape were centered and sandwiched between the second and third strips of 3M SCOTCHCAST SOFTCAST™ casting tape. The strips were laminated together by gently applying pressure by hand and the corners of the resulting laminate pad were trimmed with scissors to rounded shapes. The side with two joining layers of SCOTCHCAST SOFTCAST™ was designated the "skin side" of the laminate and the side with three joining layers of SCOTCHCAST SOFTCAST™ was designated the "top side" of the laminate. The laminate was padded by centering and pressing a strip (16 cm×25 cm) of SONTARA™ polyester nonwoven fabric (Dupont, Wilmington, Del.) to the skin side. To the top side of the laminate was centered a strip (16 cm×25 cm) of 3M RESTON™ foam (3M Company) with the non-adhesive side against the laminate. Additionally, a strip (16 cm×30 cm) of polyester felt (basis weight =238 g/m², Rogers Corporation, Rogers, Conn.) was centered and adhered to the adhesive side of the foam. The resulting water-curable shin guard was sealed overnight in a moisture-impervious foil pouch. The next day, the shin guard was removed from the pouch, wetted with water at 23 ° C., and applied to the shin by holding it in place with an elastic wrap. The curable shin guard was highly conformable and could easily be custom-fitted to the shape of the shin. The shin guard cured within three minutes to yield a custom-fitted, breathable, and protective shin guard with a hard center region and soft, flexible outer edge regions.

Various modifications and alterations of this invention will be apparent to those skilled in the art without departing from the scope and spirit of this invention, and it should be understood that this invention is not limited to the illustrative embodiments set forth herein.

What is claimed is:

1. An orthopedic casting tape, comprising:
   at least one backing; and
   at least one curable resin associated with the backing, wherein the casting tape comprises at least one longitudinally extending region of a soft casting material extending throughout the thickness of the tape along the entire length of the longitudinally extending region of soft casting material and at least one longitudinally extending region of a hard casting material.

2. The orthopedic casting tape according to claim 1, wherein the longitudinally extending region of soft casting material and the longitudinally extending region of hard casting material comprise different backings.

3. The orthopedic casting tape according to claim 2, wherein one of the backings comprises a knit fiberglass fabric.

4. The orthopedic casting tape according to claim 2, wherein the hard casting material has a TABER stiffness value greater than 90 and the soft casting material has a TABER stiffness value less than 90.

5. The orthopedic casting tape according to claim 2, wherein the hard casting material has a TABER stiffness value greater than 150, the soft casting material has a TABER stiffness value between about 5 and 75, and the casting tape has an overall ring strength greater than 80 N/cm.

6. An orthopedic casting tape, comprising:
   a first longitudinally extending region of a soft casting material extending throughout the thickness of the tape along the entire length of the longitudinally extending region of soft casting material; and
   a second longitudinally extending region of a hard casting material connected to the first region.

7. The orthopedic casting tape according to claim 6, wherein the soft casting material comprises a first extruded casting material and the hard casting material comprises a second different extruded casting material.

8. The orthopedic casting tape according to claim 6, wherein the first longitudinally extending region is between about 0.5 and 4 cm wide.

9. The orthopedic casting tape according to claim 6, wherein the first longitudinally extending region is between about 1 and 3 cm wide and forms a first edge of the casting tape.

10. The orthopedic casting tape according to claim 6, wherein the casting tape comprises two longitudinally extending regions of a soft casting material, each between about 1 and 3 cm wide, and forming first and second edges of the casting tape.

11. The orthopedic casting tape according to claim 6, wherein the hard casting material has a TABER stiffness value greater than 90 and the soft casting material has a TABER stiffness value less than 90.

12. The orthopedic casting tape according to claim 6, wherein the hard casting material has a TABER stiffness value greater than 150, the soft casting material has a TABER stiffness value between about 5 and 75, and the casting tape has an overall ring strength greater than 80 N/cm.

13. The orthopedic casting tape according to claim 7, wherein the first and second extruded casting materials comprise a thermoplastic polymer which softens or melts at temperature less than about 90° C.

14. The orthopedic casting tape according to claim 7, wherein the first and second extruded casting materials comprise a viscous curable material which can be extruded through a die and can be subsequently gelled to a state that resists flow at ambient temperatures for extended periods of time.

15. An article, comprising:

a backing; and at least one curable resin associated with the backing, wherein the article comprises a hard center region and at least one soft edge region comprising a soft casting material extending throughout the thickness of the article along the entire length of the soft edge region.

16. The article according to claim 15, wherein the backing is selected from the group consisting of knit, woven or nonwoven fabric materials and open-celled foam sheets.

17. The article according to claim 15, wherein the article comprises two different water-curable, isocyanate functional, prepolymer resins.

18. The article according to claim 15, wherein the hard center region has a TABER stiffness value greater than 90 and the soft edge region has a TABER stiffness value less than 90.

19. The article according to claim 15, wherein the article is a splint.

20. The article according to claim 19, wherein the soft edge region surrounds the periphery of a thumb hole.

21. An article selected from the group consisting of casting tapes, splints, and protective pads, the article comprising:

an apertured, extruded sheet having a plurality of extruded filaments of a material selected from the group consisting of thermoplastic polymers having a softening or melting temperature less than about 90° C. and viscous curable resins having a sufficient yield stress to resist flow at ambient temperature for extended periods of time, wherein the sheet has a sufficient number of apertures after application to the patient to allow moisture vapors produced by the skin to freely escape through the article, and wherein the apertured, extruded sheet comprises a hard region and a soft region along one or more edges of the article, wherein the soft region comprises a soft casting material extending throughout the thickness of the article along the entire length of the soft region.

22. The orthopedic casting article according to claim 21, wherein the soft region is between about 0.5 and 4 cm wide and has a TABER stiffness value less than 90, and wherein the hard region has a TABER stiffness value greater than 90.

23. A protective pad, comprising:

a backing; and at least one curable resin associated with the backing, wherein the protective pad comprises a hard center region and at least one soft edge region comprising a soft casting material extending throughout the thickness of the protective pad along the entire length of the soft edge region.

24. The protective pad according to claim 23, wherein the protective pad is custom-fitted to a portion of the human body for protection against impact injuries.

25. The protective pad according to claim 24, wherein the protective pad is selected from the group consisting of a shin guard, a thigh guard, an Achilles tendon guard, and an arm guard.

26. The protective pad according to claim 24, wherein the protective pad further comprises a padding layer.

27. The protective pad according to claim 26, wherein the padding layer is selected from the group consisting or a nonwoven material and an open-celled foam.

28. The protective pad according to claim 24, wherein the protective pad further comprises a covering.

29. The protective pad according to claim 24, wherein the protective pad further comprises means for securing to the body.

30. The protective pad according to claim 24, wherein the protective pad is flexibly connected to at least one additional protective pad to form a multiple body part protector.

* * * * *

UNITED STATES PATENT AND TRADEMARK OFFICE
CERTIFICATE OF CORRECTION

PATENT NO. : 6,595,938 B1
DATED : July 22, 2003
INVENTOR(S) : Delmore, Michael D.

It is certified that error appears in the above-identified patent and that said Letters Patent is hereby corrected as shown below:

Title page,
Item [56], References Cited, OTHER PUBLICATIONS, "stiffens" should be
-- stiffness --;

Column 4,
Line 31, insert -- 110 -- following "roll";
Line 32, insert -- 120 -- following "tape";

Column 5,
Line 40, "text" should be -- test --;

Column 7,
Line 12, "diff&rent" should be -- different --;

Column 9,
Line 58, "21431" should be -- 2143L --;

Column 10,
Lines 39-40, "dimorphiolinodiethyl" should be -- dimorpholinodiethyl --;
Line 62, "suppresser" should be -- suppressor --;

Column 11,
Line 20, "bond" should be -- bonded --;
Line 25, "are" should be -- is --;
Line 46, "Benzolphalate" should be -- Benzolphthalate --;
Line 54, "that" should be -- than --;

Column 13,
Line 66, "08/391,1 1 1" should be -- 08/391,111 --;

Column 18,
Line 17, delete "provides a" following "provides a";

Column 21,
Line 18, "provides" should be -- provide --;

Column 22,
Line 10, "A" should be -- as --;

Column 23,
Line 15, "deliniate" should be -- delineate --;

UNITED STATES PATENT AND TRADEMARK OFFICE
CERTIFICATE OF CORRECTION

PATENT NO. : 6,595,938 B1
DATED : July 22, 2003
INVENTOR(S) : Delmore, Michael D.

It is certified that error appears in the above-identified patent and that said Letters Patent is hereby corrected as shown below:

Column 24,
Line 33, "coated" should be -- coating --;

Column 26,
Line 16, "as" should be -- at --;
Line 59, insert -- below to -- following "described";
Line 65, insert -- flat onto a -- following "placed";

Column 28,
Line 4, insert -- humidity -- following "relative";
Line 28, "DBLTA" should be -- DELTA --;
Line 49, "43º C" should be -- -43º C --;

Column 30,
Line 60, insert -- a -- following "at";

Column 32,
Line 27, "or" should be -- of --.

Signed and Sealed this

Tenth Day of February, 2004

JON W. DUDAS
*Acting Director of the United States Patent and Trademark Office*